United States Patent [19]

Sayers et al.

[11] Patent Number: 5,500,344
[45] Date of Patent: Mar. 19, 1996

[54] SERINE PROTEASE AND USES THEREOF

[75] Inventors: Thomas Sayers, Boonsboro, Md.; Mark J. Smyth, Lower Plenty, Australia; Theresa A. Wiltrout, Frederick, Md.; James C. Powers, Atlanta, Ga.; Raymond Sowder, Frederick; Louis E. Henderson, Newmarket, both of Md.

[73] Assignee: The United States of America as represented by the Department of Health and Human Services, Washington, D.C.

[21] Appl. No.: 990,301

[22] Filed: Dec. 3, 1992

[51] Int. Cl.$^6$ .............................. C12Q 1/68; C12N 5/10; C12N 15/74; C07H 21/02
[52] U.S. Cl. ........................ 435/6; 435/240.2; 435/252.3; 435/320.1; 536/23.2
[58] Field of Search ........................ 435/6, 212, 320.1, 435/240.2, 252.3; 536/23.2; 935/77, 78

[56] References Cited

PUBLICATIONS

Davis et al *Basic Methods in Molecular Biology*, Elsevier, N.Y., 1986, 338 pages. ("Contents", pp. V–VIII).
*Natural Immunity* Abstracts, "Purification and Cloning of a Novel Serine Protease with MET–Ase Activity from the Granules of a Rat Natural Killer Cell Line", p. 139, Sep.–Oct. 1992.
*The FASEB Journal* Abstracts, "Purification and Characterization of the Lymphocyte Serine Protease MET–Ase–1," No. 6201, vol. 6, No. 5, Feb. 28, 1992.
*Current Opinion in Biotechnology*, 1991, 2:76–85; "Gene Probes," James C. Richards.
*The Journal of Biological Chemistry*, vol. 267, No. 34, Dec. 5, 1992, pp. 24418–24425, Smyth et al. "Purification and Cloning of a Novel Serine Protease, RNK–Met–1, from the Granules of a Rat Natural Killer Cell Leukemia."*The Journal of Immunology*, vol. 151, No. 11, Dec. 11, 1993, pp. 6195–6205, Smyth et al., "Met–ase: Cloning and Distinct Chromosomal Location of a Serine Protease Preferentially Expressed in Human Natural Killer Cells".
Odake, S., et al. *Biochemistry* 30:2217–2227 (1991).
Poe, M., et al. *J. Biol. Chem.* 266:98–103 (1991).
Hudig, D., et al. *J. Immunology* 147:1360–1368 (1991).
Fruth, U., et al. *Eur. J. Immunology* 17:1625–1633 (1987).
Poe, M., et al. *J. Biol. Chem.* 263(26):13215–13222 (1988).

Gershenfield, H. K., et al. *Proc. Natl. Acad. Sci. USA* 85:1184–1188 (1988).
Hameed, A., et al. *J. Immunology* 141:3142–3147 (1988).
Young, J. D.–E., et al. *Cell* 47:183–194 (1986).
Schmid, J. and Weissmann, C. *J. Immunology* 139:250–256 (1987).
Gershenfield, H. K. and Weissman, I. L. *Science* 232:854–858 (1986).
Lobe, C. G., et al. *Science* 232:858–861 (1986).
Brunet, J.–F., et al. *Nature* 322:268–271 (1986).
Sayers, T. J., et al. *J. Immunology* 148:292–300 (1992).
Zunino, S. J., et al. *J. Immunology* 144:2001–2009 (1990).
Shi, L., et al. *J. Exp. Med.* 175:553–566 (1992).
Zunino, S. J., et al. *Biochimica et. Biophysica Acta* 967:331–340 (1988).
Millard, P. J., et al. *J. Immunology* 132(6):3197–3204 (1984).
Nelson, R. B. and Siman, R. *J. Bio. Chem.* 265(7):3836–3843 (1990).
Tschopp, J. and Jonganeel, C. V. *Prosp. Bioch.* 27(8):2641–2646 (1988).
Ojcius, D. M., et al. *Proc. Natl. Acad. Sci. USA* 88:4621–4625 (1991).
Pasternack, M. S. and Eisen, H. N. *Nature* 314:743–745 (1985).
Lobe, C. G., et al. *Proc. Natl. Acad. Sci. USA* 83:1448–1452 (1986).
Jiang, S., et al. *Protein Exp. and Purif.* 1:77–80 (1990).
Lin, C.,–C., et al. *Cell* 51:393–403 (1987).
Jenne, D. E., et al. *Biochemistry* 28:7953–7961 (1989).
Kwon, B. S., et al. *J. Exp. Med.* 168:1839–1854 (1988).
Manyak, C. L., et al. *J. Immunology* 142:3707–3713 (1989).
Garcia–Sanz, J. A. et al. *J. Immunology* 145:3111–3118 (1990).
Jenne, D. E. and Tschopp, J. *Immuno. Rev.* 103:53–71 (1988).

*Primary Examiner*—Stephanie W. Zitomer
*Attorney, Agent, or Firm*—Morgan & Finnegan

[57] ABSTRACT

The present invention provides a purified and isolated nucleic acid molecule encoding serine protease (Met-ase) having Met-ase activity but not Asp-ase activity and a molecular weight of about 30,000 daltons on SDS PAGE under reducing and non-reducing conditions. The present invention also provides a vector comprising this nucleic acid molecule, a prokaryotic or eukaryotic host cell stably transformed or transfected with the vector, as well as a method for detecting this nucleic acid in a sample.

20 Claims, 9 Drawing Sheets

```
CTG CTG CTC CTG CTG GCC CTG AAA ACA CTG TGG GCA GTA GGC AAC AGA    48
Leu Leu Leu Leu Leu Ala Leu Lys Thr Leu Trp Ala Val Gly Asn Arg
-20              -15              -10                          -5

TTT GAG GCC CAG ATC ATT GGG GGT CGA GAG GCA GTC CCG CAC TCC CGC    96
Phe Glu Ala Gln Ile Ile Gly Gly Arg Glu Ala Val Pro His Ser Arg
                +1           5                       10

CCA TAC ATG GTC TCG CTA CAG AAT ACC AAG TCC CAC ATG TGT GGG GGA   144
Pro Tyr Met Val Ser Leu Gln Asn Thr Lys Ser His Met Cys Gly Gly
            15                  20              25

GTC CTC GTG CAT CAG AAG TGG GTG TTG ACC GCT GCC CAC TGC CTG TCT   192
Val Leu Val His Gln Lys Trp Val Leu Thr Ala Ala His Cys Leu Ser
        30                  35              40

GAA CCG CTA CAG CAG CTG AAG CTG GTG TTC GGC CTG CAC AGC CTT CAT   240
Glu Pro Leu Gln Gln Leu Lys Leu Val Phe Gly Leu His Ser Leu His
45                  50                  55                  60

GAT CCC CAA GAT CCT GGC CTT ACC TTC TAC ATC AAG CAA GCC ATT AAA   288
Asp Pro Gln Asp Pro Gly Leu Thr Phe Tyr Ile Lys Gln Ala Ile Lys
                65                  70                  75

CAC CCT GGC TAC AAC CTC AAA TAC GAG AAC GAC CTG GCC CTG CTT AAG   336
His Pro Gly Tyr Asn Leu Lys Tyr Glu Asn Asp Leu Ala Leu Leu Lys
            80                  85              90

CTG GAT GGA CGG GTG AAG CCC AGC AAG AAT GTC AAA CCA CTG GCT CTG   384
Leu Asp Gly Arg Val Lys Pro Ser Lys Asn Val Lys Pro Leu Ala Leu
        95                  100                 105

CCA AGA AAG CCC CGA GAC AAG CCT GCA GAA GGC TCC CGG TGT AGC ACG   432
Pro Arg Lys Pro Arg Asp Lys Pro Ala Glu Gly Ser Arg Cys Ser Thr
    110                 115                 120

GCT GGA TGG GGT ATA ACC CAC CAG AGG GGA CAG CTA GCC AAG TCC CTG   480
Ala Gly Trp Gly Ile Thr His Gln Arg Gly Gln Leu Ala Lys Ser Leu
125             130                 135                 140

CAG GAG CTC GAC CTG CGT CTT CTG GAC ACC CGG ATG TGT AAC AAC AGC   528
Gln Glu Leu Asp Leu Arg Leu Leu Asp Thr Arg Met Cys Asn Asn Ser
            145                 150                 155

CGC TTC TGG AAC GGT GTC CTC ACG GAC AGC ATG CTG TGC TTA AAG GCT   576
Arg Phe Trp Asn Gly Val Leu Thr Asp Ser Met Leu Cys Leu Lys Ala
        160                 165             170

GGG GCC AAG GGC CAA GCT CCT TGC AAG GGT GAC TCT GGA GGG CCC CTG   624
Gly Ala Lys Gly Gln Ala Pro Cys Lys Gly Asp Ser Gly Gly Pro Leu
        175         *       180             185
```

FIG.4A

```
GTG TGT GGC AAA GGC AAG GTG GAT GGG ATC CTG TCT TTC AGC TCC AAA    672
Val Cys Gly Lys Gly Lys Val Asp Gly Ile Leu Ser Phe Ser Ser Lys
    190             195                 200  *   *
     O                                   *

AAC TGC ACA GAC ATC TTC AAG CCC ACC GTG GCC ACT GCT GTA GCC CCC    720
Asn Cys Thr Asp Ile Phe Lys Pro Thr Val Ala Thr Ala Val Ala Pro
205  O             210           *       215                 220

TAC AGC TCC TGG ATC AGG AAG GTC ATT GGT CGC TGG TCA CCC CAG CCT    768
Tyr Ser Ser Trp Ile Arg Lys Val Ile Gly Arg Trp Ser Pro Gln Pro
                225                 230                 235

CTG ACC TGATGTCCCA AACTATCTGG ACATCATTC TTGATGTCTG GGCTGGGAA       824
Leu Thr  △

GGGACTAGGT GTGCCTCTGG GGATCAATAA ATCCTGATAT ATC                    867
```

FIG.4B

```
GATGGAGGCC TGCGTGTCTT CACTGCTGGT GCTGGCCCTG GGGGCCTGTC AGTAGGCAGC   60

TCCTTTGGGA CCCAG ATC ATC GGG GGC CGG GAG GTG ATC CCC CAC TCG CGC  111
                 Ile Ile Gly Gly Arg Glu Val Ile Pro His Ser Arg
                  1           5                   10

CCG TAC ATG GCC TCA CTG CAG AGA AAT GGC TCC CAC CTG TGC GGG GGT  159
Pro Tyr Met Ala Ser Leu Gln Arg Asn Gly Ser His Leu Cys Gly Gly
         15                  20                  25

GTC CTG GTG CAC CCA AAG TGG GTG CTG ACG GCT GCC CAC TGC CTG GCC  207
Val Leu Val His Pro Lys Trp Val Leu Thr Ala Ala His Cys Leu Ala
         30                  35                  40

CAG CGG ATG GCC CAG CTG AGG CTG GTG CTG GGG CTC CAC ACC CTG GAC  255
Gln Arg Met Ala Gln Leu Arg Leu Val Leu Gly Leu His Thr Leu Asp
 45                  50                  55                  60

AGC CCC GGT CTC ACC TTC CAC ATC AAG GCA GCC ATC CAG CAC CCT CGC  303
Ser Pro Gly Leu Thr Phe His Ile Lys Ala Ala Ile Gln His Pro Arg
                     65                  70                  75

TAC AAG CCC GTC CCT GCC CTG GTG TTC GAC CTC GCG CTG CTT CAG CTG  351
Tyr Lys Pro Val Pro Ala Leu Val Phe Asp Leu Ala Leu Leu Gln Leu
                 80                  85                  90

GAC GGG AAA GTG AAG CCC AGC CGG ACC ATC CGG CCG TTG GCC CTG CCC  399
Asp Gly Lys Val Lys Pro Ser Arg Thr Ile Arg Pro Leu Ala Leu Pro
             95                 100                 105

AGT AAG CAC CAG GTG GTG GCA GCA GGG ACT CGG TGC AGC ATG GCC GGC  447
Ser Lys His Gln Val Val Ala Ala Gly Thr Arg Cys Ser Met Ala Gly
         110                 115                 120

TGG GGG CTG ACC CAC CAG GGC GGG GGC CTG TCC CGG GTG CTT GCG GAG  495
Trp Gly Leu Thr His Gln Gly Gly Gly Leu Ser Arg Val Leu Ala Glu
125                 130                 135                 140

CTG GAC CTC CAA GTG CTG GAC ACC CGC ATG TGT AAC AAC AGC CGC TTC  543
Leu Asp Leu Gln Val Leu Asp Thr Arg Met Cys Asn Asn Ser Arg Phe
                 145                 150                 155

TGG AAC GGC AGC CTC TCC CCC AGC ATG GTC TGC CTG GCC GCC GAC TCC  591
Trp Asn Gly Ser Leu Ser Pro Ser Met Val Cys Leu Ala Ala Asp Ser
             160                 165                 170

AAG GAC CAG GCT CCC TGC AAG GGT GAC TCG GGC GGG CCC CTG GTG TGT  639
Lys Asp Gln Ala Pro Cys Lys Gly Asp Ser Gly Gly Pro Leu Val Cys
         175                 180                 185
```

FIG.6A

```
GGC AAA GGC CGG GTG TTG GCC GGA GTC CTG TCC TTC AGC TCC AGG GTC    687
Gly Lys Gly Arg Val Leu Ala Gly Val Leu Ser Phe Ser Ser Arg Val
    190             195             200

TGC ACT GAC ATC TTC AAG CCT CCC GTG GCC ACC GCT GTG GCG CCT TAC    735
Cys Thr Asp Ile Phe Lys Pro Pro Val Ala Thr Ala Val Ala Pro Tyr
205             210             215                 220

GTG TCC TGG ATC AGG AAG GTC ACC GGC CGA TCG GCC TGATGCCCTG GGGT    785
Val Ser Trp Ile Arg Lys Val Thr Gly Arg Ser Ala
                225             230

GATGGGGACC CCCTCGCTGT CTCCACAGGA CCCTTCCCCT CCAGGGGTGC AGTGGGGTGG  845

GTGAGGACGG GTGGGAGGGA CAGGGAGGGA CCAATAAATC ATAATGAAGA AACGCTCAAA  905

AAAAAAAAAA AAAAAAAAA                                               925
```

FIG.6B

SERINE PROTEASE AND USES THEREOF

BACKGROUND OF THE INVENTION

Cell-mediated killing by cytotoxic lymphocytes is an important immunologic defense against tumor cell proliferation, viral infection and transplanted tissue (Duke, R. C., et al. *J. Exp. Med.* 170:1451–1456 (1989)). Cytotoxic lymphocyte—mediated lysis is often associated with the formation of membrane lesions on target cells caused by exocytosis of cytoplasmic granules from cytolytic lymphocytes (Henkart, P. A., et al. *J. Exp. Med.* 160:75–93 (1984); Joag, S., et al. *J. Cell Biochem.* 39:239–252 (1989)).

These granules contain proteoglycans (MacDermott, R. P., et al. *J. Exp. Med.* 162:1771–1787 (1985)) and several proteins (Tschopp, J., and Johngeneel, C. V. *Biochemistry* 27:2641–2646 (1988); Shinkai, Y., et al. *Nature* 334:525–527 (1988); Lichtenheld, M. G., et al. *Nature* 335:448–451 (1988); Tschopp, J., and Nabholz, M. *Annu. Rev. Immunol.* 8:279–302 (1990); Liu, C-C., et al. *Cell* 51:393–403 (1987); Tian, Q., et al. *Cell* 67:629–639 (1991)), including serine proteases (SP) (Tschopp, J., and Johngeneel, C. V. *Biochemistry* 27:2641–2646 (1988)) and pore-forming protein (cytolysin) (PFP) (Shinkai, Y., et al. *Nature* 334:525–527 (1988); Lichtenheld, M. G., et al. *Nature* 335:448–451 (1988); Tschopp, J., and Nabholz, M. *Annu. Rev. Immunol.* 8:279–302 (1990)). PFP forms transmembrane ionic pores that produce membrane damage (Young, J. D. *Physiol. Rev.* 69:250–314 (1989); Ojcius, D. M., et al. *Proc. Natl. Acad. Sci. USA* 88:4621–4625 (1991)) but does not cause DNA fragmentation (Duke, R. C., et al. *J. Exp. Med.* 170:1451–1456 (1989)).

A direct role for SP in cytolysis has not been universally accepted (Henkart, P. A., et al. *J. Immunol.* 139:2398–2405 (1987); Berke, G. *Immunol. Lett.* 20:169–178 (1989); Ostergaard, H. L. and Clark, W. L. *J. Immunol.* 143:2120–2126 (1989)), despite the fact that a number of protease inhibitors can block cytotoxic T lymphocyte (CTL) —mediated lysis (Chang, T. W., and Eisen, J. E. *Nature* 124:1028–1033 (1980); Hudig, D., et al. *J. Immunol.* 147:1360–1368 (1991)). DNA fragmenting properties have been postulated for two members of the SP family (Munger, W. E., et al. *Immunol. Rev.* 103:99–109 (1988); Shi, L., et al. *J. Exp. Med.* 175:553–566 (1992)) when combined with PFP. Alternatively, it has been suggested that granules break down various extracellular matrix proteins (Simon, M. M., et al. *Immunol.* 60:219–230 (1987); Sayers, T. J., et al. *J. Immunol.* 148:292–300 (1992)) and may therefore be involved in the in vivo trafficking of NK cells and CTL or in modifying effector cell:target interactions.

Several serine protease genes from CTL and NK cells have been isolated and sequenced by several different laboratories (Zunino, et al. *Biochem. Biophys. Acta.* 967:331–340 (1988); Lobe, C. G., et al. *Proc. Natl. Acad. Sci. USA* 83:1448–1452 (1986); Lobe, C. G., et al. *Science* 232:858–861 (1986); Gershenfeld, H. K., and Weissman, I. L. *Science* 232:854–858 (1986); Jenne, D. E., and Tschopp, J. *Immunol. Rev.* 103:53–71 (1988); Brunet, J-F., et al. *Nature* 322:268–271 (1986); Kwon, B. S., et al. D-E. *J. Exp. Med.* 168:1839–1854 (1988); Schmid, J., and Weissman, C. *J. Immunol.* 139:250–256 (1987); Gershenfeld, H. K., et al. *Proc. Nat'l Acad. Sci. USA* 85:1184–1185 (1988); Manyak, C. L., et al. *J. Immunol.* 142:3703–3713 (1989); Zunino, S. J., et al. *J. Immunol.* 144:2001–2009 (1990)).

Some of these cDNAs encode the same protein, but seven different serine proteases have been identified. Seven serine proteases, granzymes A, B, C, D, E, F, and G, have been isolated and purified from murine granules (Maseon, D. and Tschopp, J. *Cell* 49:679–685 (1987)). Murine granzyme A is also known as Hanukah factor (Gershenfeld, H. K., and Weissman, I. L. *Science* 232:854–858 (1986)), TSP-1 (Simon, M. M., et al. *Immunol.* 60:219–230 (1987)), BLT-esterase (Pasternak, M. S., et al. *Nature* 314:743–745 (1985)), CTLA-3 (Brunet, J-F., et al. *Nature* 322:268–271 (1986)); and SE1 (Young, J. E.-E., et al. *Cell* 47:183–194 (1986)); murine granzyme B as CCP1 (Lobe, C. G., et al. *Science* 232:858–861 (1986)); and CTLA-1 (Brunet, J-F., et al. *Nature* 322:268–271 (1986)); granzyme C (Masson, D. and Tschopp, J. *Cell* 49:679–685 (1987)) as CCP2 (Lobe, C. G., et al. *Science* 232:858–861 (1986)); granzyme E as CCP3 (Bleackley, et al. *FEBS Lett.* 234:153–159 (1988)); and granzyme F as CCP4 (Bleackley, et al. *FEBS Lett.* 234:153–159 (1988)).

Granzymes A and B also have been isolated from human CTL granules and are homologous to the murine enzymes (Fruth, U., et al. *Eur. J. Immunol.* 17:1625–1633 (1987); Poe, M., et al. *J. Biol. Chem.* 266:98–103 (1991)). Human granzyme A is also known as HuTSP (Fruth, U., et al. *Eur. J. Immunol.* 17:1625–1633 (1987)), Hanukah factor (Gershenfeld, H. K., et al. *Proc. Nat'l Acad. Sci. USA* 85:1184–1185 (1988)), CTL tryptase (Poe, M., et al. *J. Biol. Chem.* 263 (26):13215–13222 (1988)), and granzyme 1 (Hameed, A., et al. *J. Immunol.* 141:3142–3147 (1988)); and human granzyme B as HLP (Schmid, J., and Weissman, C. *J. Immunol.* 139:250–256 (1987)), HSE26.1 (Trapani, J. A., et al. *Proc. Nat'l. Acad. Sci. U.S.A.* 85:6924–6928 (1988)), SECT (Caputo, A., et al. *J. Biol. Chem.* 263:6363–6369 (1988)), granzyme 2 (Hameed, A., et al. *J. Immunol.* 141:3142–3147 (1988)), and Q31 granzyme B (Poe, M., et al. *J. Biol. Chem.* 266:98–103 (1991)). Only one rat granzyme, RNKP-1, has been purified (Sayers, T. J., et al. *J. Immunol.* 148:292–300 (1992)) and sequenced (Zunino, S. J., et al. *J. Immunol.* 144:2001–2009 (1990)).

Thus far, the hydrolytic activities for only three enzymes, Tryptase, Chymase, and ASP-ase, encoded by the seven serine protease genes have been described. Granzymes A and F have been shown to exhibit tryptase activity (Jenne, D. E., and Tschopp, J. *Immunol. Rev.* 103:53–71 (1988); Jiang, S., et al. *Protein Expression Purification* 1:77–85 (1990)); granzyme B has shown predominantly ASP-ase activity and some Met-ase activity (Odake, S., et al. *Biochemistry* 30:2217–2227 (1991); Poe, M., et al. *J. Biol. Chem.* 266:98–103 (1991)); and granzymes D, E, and F were predicted to have chymase activity (Odake, S., et al. *Biochemistry* 30:2217–2227 (1991)). Granzymes C and G, although tested, have not been shown to exhibit a specific enzymatic activity (Odake, S., et al. *Biochemistry* 30:2217–2227 (1991)). RNKP-1 has been shown to have ASP-ase activity.

With respect to the Met-ase activity exhibited by granzyme B, Odake, et al. suggested that this activity may belong to granzyme B because of the observation that the Met-ase and Asp-ase activities coelute from the Mono S column and the nearly identical inhibition rates of granzyme B with DCI when three different substrates are used. On the other hand, Odake, et al. stated that the observation by Poe, et al. (Poe, M., et al. *J. Biol. Chem.* 266:98–103 (1991)) that the Met-ase activity was separated from the Asp-ase activity during the purification of human granzyme B suggests the presence of different enzymes.

Other than granzyme B, no cytolytic granule proteins have been reported which exhibit Met-ase activity.

This invention describes the biochemical purification of a novel 30 kDa SP with Met-ase activity (RNK Met-1) from the cytolytic granules of the rat RNK-16 LGL leukemia. Isolation and sequencing of the cDNA encoding RNK Met-1 from a rat RNK-16 λgt-11 library reveals RNK Met-1 to be a unique SP gene with structural variations that distinguish it from other members of the SP family. The invention also describes the human serine protease and its cDNA clone obtained by screening the phage λgt-10 cDNA library from human Lopez LGL leukemia with the rat RNK-Met-1 cDNA clone.

SUMMARY OF THE INVENTION

The present invention provides a purified and isolated nucleic acid molecule encoding serine protease (Met-ase) having Met-ase activity but not Asp-ase activity and a molecular weight of about 30,000 daltons on SDS PAGE under reducing and non-reducing conditions. The present invention also provides a vector comprising this nucleic acid molecule, a prokaryotic or eukaryotic host cell stably transformed or transfected with the vector, as well as a method for detecting this nucleic acid in a sample.

DESCRIPTION OF THE FIGURES

FIGS. 4A and 4B. Nucleotide and predicted amino acid sequences (SEQ ID NO:1 and SEQ ID NO:2, respectively) of RNK-Met-1. Nucleotide sequence is numbered from the first nucleotide of the cloned 867 bp cDNA insert. Amino acid sequence encoded by this clone is shown by standard abbreviations below the respective DNA sequence. The numbering of the amino acid sequence starts with the amino-terminal residue (+1) of the mature RNK-Met-1 protein as determined by amino acid sequencing. The partial protein sequence determined for the amino terminus of RNK-Met-1 is underlined. The residues forming the catalytic site of SP are boxed (□) and all cysteine residues are circled (○). The putative N-linked glycosylation sites are marked by dashed underline (---) and the combination of amino acid residues thought to determine the specificity of the substrate binding pocket are asterisked (*). The stop codon is denoted (Δ) and polyadenylation signal sequence in the 3' non coding region is underlined.

FIG. 5A; (1) rat $CRC^+$ RNK-16 NK leukemia (in vitro), (2) rat $CRC^-$ RNK-16 NK leukemia (in vitro), (3) normal rat liver, (4) normal rat colon, (5) normal rat brain, (6) rat RNK-16 NK leukemia (in vivo—passage 7), (7) human HuT 78 T cell lymphoma, (8) human YT LGL leukemia (9) gibbon MLA 144 lymphoma, (10) mouse CTLL R8 cytotoxic T cell clone, (11) human Lp NK leukemia and (12) mouse P815 mastocytoma; FIG. 5B; (1) normal rat spleen (unseparated), (2) normal rat splenocytes (nylon wool passed), (3) normal rat thymocytes, (4) normal rat thymocytes treated with PMA (20 ng/ml) and IL-2 (1000 U/ml) for 4 days and (5) normal rat A-LAK splenocytes (see Materials and Methods). Northern blot analysis was performed on 25 µg of RNA and the filters were sequentially hybridized with $^{32}P$-labeled cDNA probes for: rat RNK-Met-1 (exposure, 2 days) and human γ-actin (exposure, 1 day).

FIGS. 6A and 6B. Nucleotide and predicted amino acid sequences (SEQ ID NO:3 and SEQ ID NO:4, respectively) of human Met-ase.

DETAILED DESCRIPTION OF THE INVENTION

Figure 1A:
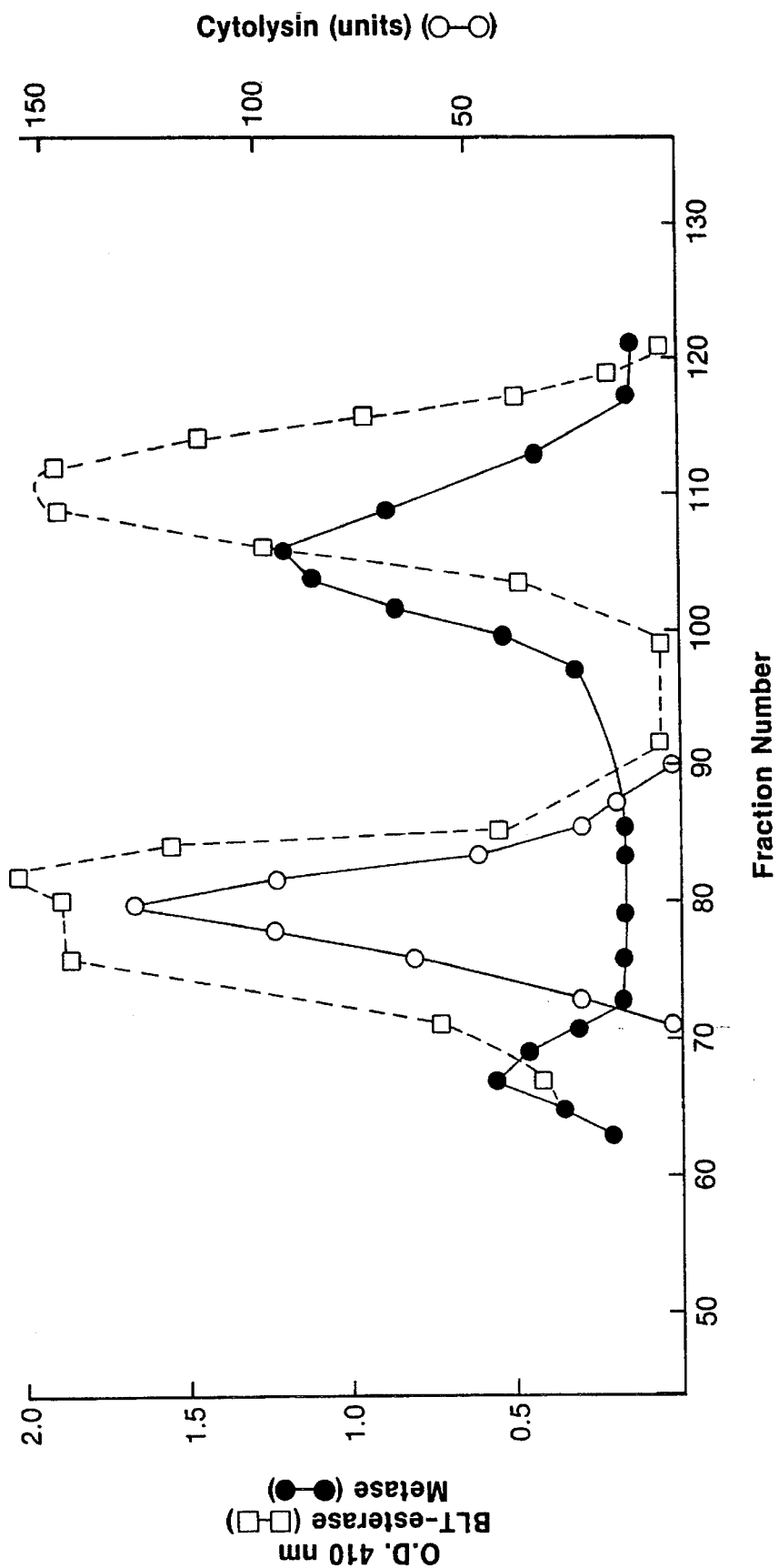
FIGS. 1A and 1B. Separation of granule constituents on an ACA 54 column. Fractions were extensively dialysed against PBS and tested for BLT-esterase activity (□—□) or Met-ase activity (●—●) by assaying the change in $O.D._{410}/10$ min caused by 50 µl of each fraction (FIG. 1A). Cytolysin (PFP) activity (○—○) in units/ml was assayed as described in the Materials and Methods (FIG. 1A). The elution peaks of molecular weight markers were fractions 79 (BSA, 67 kDa), 93 (ovalbumin, 43 kDa), 121 (chymotrypsinogen, 25 kDa) and 134 (ribonuclease, 13.7 kDa). The O.D.280nm ranged from 0.00– 0.02 (FIG. 1B).

The present invention provides a purified and isolated serine protease (Met-ase) having Met-ase activity but not Asp-ase activity and a molecular weight of about 30,000 daltons on SDS PAGE under reducing and non-reducing conditions.

The protease of the present invention is purified to homogeneity sufficient to be sequenced and is at least about 90% pure. At this purity level, the protease has a Met-ase activity of about 156 nM/sec/µg without the intentional addition of other substances such as other proteins or carriers. The assay for measuring this activity was performed as described in the Experimental Details section. The specific activity, however, depends on the degeneracy and folding of the protease and may be as low as about 100 nM/sec/µg to as high as about 200 nM/sec/µg.

In the preferred embodiment, the protease has the amino acid sequence selected from the group consisting of: (a) the amino acid sequence contained in FIGS. 4A and 4B (SEQ ID NO:2); (b) the amino acid sequence contained in FIGS. 6A and 6B (SEQ ID NO:4); and (c) biologically active fragments or analogs of the amino acid sequence defined in (a) or (b). The serine protease of the present invention encompasses both the rat and human forms as well as proteases having the same characteristics and Met-ase activity from other mammalian sources.

The present invention also provides a purified and isolated DNA molecule comprising a DNA sequence encoding the protease hereinabove. The DNA molecule includes all DNA sequences which encode for the protease including all degenerate forms. In the preferred embodiment, the DNA molecule comprises a DNA sequence selected from the group consisting of: (a) the DNA sequence contained in FIGS. 4A and 4B (SEQ ID NO:1) or a complementary strand thereof; (b) the DNA sequence contained in FIGS. 6A and 6B (SEQ ID NO:3) or a complementary strand thereof; (c) DNA sequences which hybridize to the DNA sequence defined in (a) or (b), or fragments thereof; and (d) DNA sequences, but for the degeneracy of the genetic code, would hybridize to the DNA sequences defined in (a), (b), or (c).

The present invention also provides an antibody immunoreactive with the protease hereinabove. The antibody may be polyclonal or monoclonal. If polyclonal, the antibody may be produced by immunizing a rabbit, mouse or rat with the protease or fragment thereof as an immunogen and collecting the serum produced thereby. The protease or fragment therof may be coupled to a protein such as keyhole limpet hemocyanin (KLH) or bovine serum albumin (BSA), with or without an adjuvant. A booster injection should be give 4–6 weeks after the primary injection. Additional booster injections may be given at later periods if necessary. The presence of antibody in the serum may be tested by radioimmunoassay (RIA), enzyme-linked immunosorbent assay (ELISA), or immunoprecipitation. To produce monoclonal antibodies, the spleen cells from the rabbit, mouse or rat are removed and fused with a myeloma cell, grown in culture, then inserted into a hybridoma to produce the desired monoclonal antibody by standard procedures.

The antibody of the present invention may then be used in detecting the protease in a sample or in the purification of recombinant protease from a recombinant host. For detection purposes, the antibody may be labeled with a detectable marker, including but not limited to a fluorescence, enzyme or radiolabeled marker known to those skilled in the art. The labeled antibody (polyclonal or monoclonal) may then be used to detect the protease of the present invention in a biological sample by using standard technology such as solid phase radioimmunoassay (e.g. competition RIAs, immobilized antigen or antibody RIAs, or double antibody RIAs), immunoprecipitation, or Western blotting.

The present invention also provides a method for detecting nucleic acid encoding the protease hereinabove (Metase) in a sample which comprises contacting nucleic acid from the sample with the DNA molecule hereinabove labeled with a detectable marker (as described above) under conditions permitting the nucleic acid to hybridize with the labeled DNA molecule, determining that hybridization has occurred, and thereby detecting nucleic acid encoding Metase in the sample.

The sample is a biological cell tissue or fluid sample from a mammalian subject and preferably is human. The sample is preferably from a tumor and is removed by standard biopsy procedures. The nucleic acid from the sample is then removed by procedures known to those in the art such as phenol/chloroform/ethanol extraction or guanidine thiocyanate. The nucleic acid may be DNA or RNA.

The labeled DNA molecule is contacted with the nucleic acid from the sample under hybridizing conditions. Hybridization of the two nucleic acids is determined by procedures known to those skilled in the art and is a function of the marker employed (e.g. fluorescent, enzyme or radiolabeled marker). The protease is detected in the sample when hybridization has occurred.

The protease also may be detected in the sample using polymerase chain reaction (U.S. Pat. Nos. 4,683,200 and 4,683,195 and Perkin Elmer/Cetus kit). The oligonucleotide primers based on the DNA sequence hereinabove are synthesized by standard techniques (e.g. H-phosphate method, dideoxy method, etc.). If the nucleic acid from the sample is RNA, it must first be converted to cDNA using reverse transcriptase (Perkin Elmer/Cetus Reverse Transcriptase kit). The DNA or CDNA is then subjected to PCR amplification using the synthesized primers. The protease is present in the sample if PCR amplification occurs.

Following PCR, the presence of the protease may be detected further using electrophoresis or other techniques.

The present invention also provides the protease hereinabove produced by recombinant techniques (see U.S. Pat. Nos. 4,704,362, 4,366,246, 4,425,437, 4,356,270, and 4,571,421). Specifically, the protease DNA is placed into a vector (e.g. plasmid, bacteriophage λ, or cosmid vector) by standard techniques. The vector containing the protease DNA is then stably tranformed or transfected in a microbial mammalian expression system which recombinantly produces the protease. The expression system is preferably a prokaryotic (pGEX, pPOW) or eukaryotic (CDM8, pSVL, vaccinia, or baculovirus) cell host. The host cells are then screened for clones which produce the recombinant serine protease. The present invention also provides a recombinant DNA molecule comprising the DNA molecule hereinabove operably linked to an expression-linked control sequence.

The following Experimental Details Section sets forth specific examples to aid in an understanding of the invention, and should not be construed to limit in any way the invention as defined in the claims which follow thereafter.

Experimental Details

A. Materials and Methods.

Abbreviations: SP, serine protease; LGL, large granular lymphocyte(s); PFP, pore-forming protein (cytolysin); Hepes, N-2-hydroxyethylpiperazine-N'-2-ethane sulfonic acid; BLT, α-N-benzloxycarbonyl-L-lysinethiobenzylester; DTNB, 5,5'- dithiobis-(2-nitrobenzoic acid); Bzl, benzyl; PCR, polymerase chain reaction; PMA, phorbol myristate acetate; PEG, polyethylene glycol.

Rats/RNK tumors. Tumor cells from the rat large granular lymphocyte leukemia (RNK) were kindly provided by Dr. C. Reynolds (BRMP, FCRDC, Frederick, MD). RNK tumors were serially passaged in vivo in Fischer (F344) rats. Most of the tumor cells were from the RNK-16 line (passages 6–13) in ascites form.

Purification of Cytoplasmic Granules. The procedure for purification of cytoplasmic granules of rat LGL tumors has previously been described in detail (Millard, P. J., et al. *J. Immunol.* 132:3197–3204 (1984)). Briefly, RNK cells ($5 \times 10^9$–$1 \times 10^{10}$) were washed in Hank's balanced salt solution (HBSS) and resuspended at $1 \times 10^8$ cells/ml in disruption buffer (0.25M Sucrose, 0.01M N-2-hydroxyethylpiperazine-N'-2-ethane sulfonic acid (Hepes), 4 mM EGTA, 1000 U/ml Heparin [Sigma Chemical Co., St. Louis, Mo.] pH7.4). Cells were lysed by decompression at 0° C. after equilibrating at 450 psi nitrogen for 20 min. After the addition of $MgCl_2$ to 5 mM, the homogenate was digested with DNase 1 (800 μ/ml, 22° C., 30 min). Nuclei were removed by filtration through Nucleopore filters (Nucleopore Corp., Pleasanton, Calif.) of 5 and 3μm and the resulting homogenate was cooled at 0° C. Aliquots of 5 ml were layered onto 20 ml of 48% Percoll (in disruption buffer without heparin) and centrifuged on a 50.2 Ti rotor at 29,000 rpm (70,000 g) for 30 min at 4° C. on a Beckman L 5–50B ultracentrifuge (Beckman Instruments, Fullerton, Calif.). Fractions (1 ml) of purified granules were localized to a visible band near the bottom of the tubes. The success of fractionation was monitored by assaying α-N-benzyloxycarbonyl-L-lysine-thiobenzylester (BLT)-esterase activity and the granule containing fractions were pooled and Percoll removed by centrifugation (100,000 g, 3 h). Granules were recovered as a loose white pellet over a hard Percoll pellet and stored at −70° C.

Purification of Granule RNK Met-1. Dense granules combined from 6–10 isolations were solubilized by suspension in 2M NaCl to give a final volume of 20 ml in ACA column buffer (PBS diluted 1:1 with 10 mM Hepes, pH 7.4 containing 2M NaCl, 0.5 mM EGTA). The mixture was rapidly freeze—thawed twice and subjected to centrifugation (100,000 g, 3 h) to remove insoluble material. This extract was sterile filtered through a 0.45μm Nalgene filter (Nalge Company, Rochester, N.J.) and concentrated to a total volume of 10–15 ml using centricon 10 concentrators (Amicon, Danvers, Mass.) that have a molecular weight cut-off of 10 kD. The soluble extract was fractioned by gel filtration on an Ultrogel ACA 54 column (IBF Biotechnics Inc., Savage, Md.) 80 cm×5 cm and 8 ml fractions were collected. Fractions were concentrated and extensively dialyzed against PBS, pH7.2 (Spectra/Por 7, Spectrum Medical Industries Inc., Los Angeles, Calif.) (cut off 15 kDa). Individual fractions were then tested for protease activity, BLT-esterase activity, and cytolysin activity (see below). Column fractions containing the majority of the granule Met-ase activity were pooled and concentrated to about 4 mls (Centricon 10). The pooled Met-ase activity was exhaustively dialyzed against PBS, 0.2% polyethylene glycol (PEG) and further purified by heparin—agarose affinity chromatography (Pierce, Rockford, Ill.). A 1 ml prepacked column was equilibrated with PBS, 0.2% PEG, pH7.2 and then stepwise elutions were performed with column buffer containing 0.1, 0.3, 0.65 and 0.8M NaCl (~15 ml/elution). Fractions were made up to 30 ml with PBS, 0.2% PEG, 2M NaCl and concentrated to 2–4 ml (Centricon 10). Aliquots from each elution were extensively dialyzed against PBS and tested for BLT—esterase and protease activity.

Fractions containing the granule Met-ase activity were made up to 0.04M Tris-HCl., pH 7.4 by the addition of concentrated buffer, and 8M guanidine (Pierce). The resulting solution was injected onto a high-pressure liquid chromatograph (Waters Associates, Milford, Mass.) and separated by reverse phase HPLC on a μ-Bondapak C18 column (Waters Associates) as previously described (Henderson, L. E., et al. *J. Virol.* 52:492–500 (1984)). The column was equilibrated in 0.05% trifluoroacetic acid (TFA) and proteins were eluted using a linear gradient of acetonitrile and 0.05% TFA. Eluted proteins were detected by UV absorption at 206 nm with a model 2140 Rapid Spectral detector (LKB, Bromina, Sweden) and 2 ml fractions were collected. A small volume of BSA was added to aliquots from the HPLC column (100 μg/ml) for stabilization. Solvents were removed by lyophilization. The lyophilate was reconstituted in PBS, 20% glycerol, pH 7.2 and dialyzed extensively against this buffer to promote protein renaturation. Aliquots were extensively dialyzed against PBS and tested for BLT-esterase and protease activity.

Gas-Phase Sequencing. Amino acid sequences were determined by the Edman degradation procedure as previously described (Hewick, R. M., et al. *J. Biol. Chem.* 256:7990–7997 (1981)) using a model 470 A Protein Sequencer (Applied Biosystems, Foster City, Calif.).

Gel Electrophoresis. Sodium dodecyl sulfate (SDS)-polyacrylamide electrophoresis (PAGE) was performed on 4–20% gradient gels (Novex, Encinitas, Calif.) by the method of Laemmli (Laemmli, V. K. *Nature* 227:680–685 (1970)). Proteins were visualized by 0.5% Coomassie Brilliant blue in 40% methanol/10% acetic acid. Low levels of protein were detected using silver staining (Daiichi Pure Chemicals Co., Ltd. Hyde Park, Mass.).

Assay of Proteases. Thiobenzylester substrates were used to measure protease activities. For monitoring enzyme activities from granules and column fractions, assays were performed at room temperature using 0.5 mM 5,5'-dithiobis-(2-nitrobenzoic acid) (DTNB) (Sigma) to detect the HSBzl leaving group ($e_{410}=13600M^{-1}cm^{-1}$).

BLT-esterase activity was estimated using a microtiter assay (Green, G. D. J., and Shaw, E. *Anal. Biochem.* 93:223–226 (1979)). Briefly, 50 μl of sample was added to 100 μl of 1 mM DTNB, made up in 10 mM Hepes, 1 mM $CaCl_2$, 1 mM $MgCl_2$, pH7.2. The reaction was initiated by the addition of 50 μl of BLT (Sigma) to give a final concentration of 500 μM. For Metase determinations, 50 μl of dilutions of the sample in 0.1M Hepes, 0.05M $CaCl_2$, pH7.5 were added to 100 μl of 1 mM DTNB and the reaction was initiated by the addition of 50 μl of Boc-Ala-Ala-Met-S Benzyl (Bzl) to give a final concentration of 150 μM. The duration of the assay depended on color development, the rate of which was measured ($0.D_{410}$) on a Dynatech MR 5000 microplate reader. Controls of sample and DTNB alone or DTNB and substrate alone were run. For more sensitive comparisons of enzymatic activities, peptide thiobenzyl ester substrates were used to measure protease activities. The chymase substrate Suc-Phe-Leu-Phe-SBzl was purchased from BACHEM Bioscience Inc., Philadelphia, Pa. Z-Arg-SBzl (the tryptase substrate, Kam, C-M., et al. *J. Biol. Chem.* 262:3444–3451 (1987)); Boc-Ala-Ala-AA-SBzl (AA=Asp, Met, Leu, Nle, or Ser) and Suc-Ala-Ala-Met-SBzl (Odake, S., et al. *Biochemistry* 30:2217–2227 (1991); Harper, J. W., et al. *Biochemistry* 23:2995–3002 (1984)) were synthesized previously. Boc-Ala-Ala-Asp-SBzl is the substrate for Asp-ase and peptide thiobenzyl esters containing Met, Leu or Nle are substrates for Met-ase SP. Assays were performed at room temperature in 0.1M, Hepes buffer, pH7.5, containing 0.01M $CaCl_2$ and 8% $Me_2SO$ using 0.34 mM 4,4'-dithiodipyridine (Aldrithiol-4, Aldrich Chemical Co., Milwaukee, Wis.) to detect HSBzl leaving group that reacts with 4,4'-dithiodipyridine to release thiopyridone ($\epsilon 324=19800M^{-1}cm^{-1}$, Grasetti, D. R. and Murray, J. F. *Arch. Biochem. Biophys.* 119:41–49 (1967)). The initial rates were measured at 324 nm using a Beckman 35 spectrophotometer when 10–25 μl of an enzyme stock solution was added to a cuvette containing 2.0 ml of buffer, 150 μl of 4,4'-dithiodipyridine and 25 μl of substrate. The same volume of substrate and 4,4'-dithiodipyridine were added to the reference cell in order to compensate for the background hydrolysis rate of the substrates. Initial rates were measured in duplicate for each substrate concentration and were averaged in each case. Substrate concentrations were 100–133 μM.

Cytolysin assays. Cytolysin (PFP) activity was measured using sheep E as targets (Henkart, P. A., et al. *J. Exp. Med.* 160:75–93 (1984)).

Screening of cDNA library. Two oligonucleotide primers were synthesized to PCR amplify a RNK-Met-1 cDNA probe from RNK-16 total cellular RNA. The 5'–3' primer was a degenerate inosine containing 41 mer (5'GAATTC-.TAC(T)ATG GTI TCI CTI CAA(G) AAC(T) ACI AAA(G) TCI GAC(T) GT3') (SEQ ID NO:5 AND SEQ ID NO:6) coding for the Tyr-Met-Val-Ser-Leu-Gln-Asn-Thr-Lys-Ser-His-Met (pos. 14–25) (SEQ ID No:7) unique region obtained from sequencing the first 25 N-terminal amino acids of the RNK-Met-1 protein. The 3'–5'primer was a 21 mer (3'CTG AGA CCT CCC GGA.CTTAAG 5') (SEQ ID NO:8) coding for the Asp-Ser-Gly-Gly-Pro (SEQ ID NO:9) amino acid sequence around the active site Ser (pos. 183–187) that is conserved in SP proteins. EcoRI ends were included in these oligonucleotide primers for subcloning. Total cellular RNA was isolated as described below. RNA (1 μg) was made up to 20 μl in a reaction mixture [10 mM Tris-HCl buffer, pH 8.3, 50 mM KCl (Perkin-Elmer Cetus (PE-Cetus), Norwalk, Conn.) 5 mM $MgCl_2$, 150 pmol random hexamers (Pharmacia Inc., Piscataway, N.J.), 200 U Murine Moloney Virus H Reverse Transcriptase (Bethesda Research Laboratories (BRL), Gaithersburg, Md.), 20 U RNAsin (Promega Corp., Madison, Wis.), and 1 mM of each dNTP]. cDNA synthesis was performed at 42° C. for 15 min, 99° C. for 5 min and 5° C. for 5 min. For PCR amplification, samples were made up to a final 100 µl reaction mixture (10 mM Tris-HCl buffer, pH 8.3, 50 mM KCl, 2 mM $MgCl_2$, 100 pmol of both primers and 2 U Taq DNA polymerase (PE-Cetus)). Thirty PCR cycles were run for 1 min at 94° C., 2 min at 50° C., and 3 min at 72° C. The PCR products were analyzed on a 3% NuSieve gel(FMC Bioproducts, Rockland, Me.). A 534 bp fragment amplified specifically from RNK-16 mRNA was gel purified on a DEAE cellulose membrane and subcloned into the EcoRI site of the vector pBluescript $KS^+$.

This fragment was used to screen a RNK-16 cDNA library to isolate a full length clone. The cDNA library was made from rat RNK-16 tumor cell RNA at the National Institutes of Health (Bethesda, Md.) by Dr. Cho Yue using the Gubler and Hoffman method of cDNA synthesis (Gubler, U., and Hoffman, B. J. *Gene* 25:263–269 (1983)). Sequencing was performed in both orientations using the dideoxy method (Sanger, F., et al. *Proc. Natl. Acad. Sci. USA* 74:5463–5467 (1977)) and single stranded and double stranded templates (Chen, E. Y. and Seeburg, P. H. *DNA* 4:165–170 (1985)).

*Northern Blot Analysis.* Total cellular RNA was obtained from the following cell lines and tissues; murine P815 mastocytoma, murine CTLL-R8 cytotoxic T cell clone, human Lp NK leukemia, gibbon MLA 144 lymphoma, HuT 78 human T cell lymphoma, human U937 histiocytic lymphoma and the human YT LGL leukemia. Cells were cultured in RPMI 1640 medium supplemented with 10% heat-inactivated fetal calf serum, 2 mM glutamine, 100 U/ml penicillin and 100 µg/ml streptomycin (Gibco Laboratories, Life Technologies, Grand Island, N.Y.). The in vitro RNK16 cell lines, $CRC^+$ and $CRC^-$ were cultured in the above medium supplemented with $5\times10^{-5}$M 2-ME (Sigma) and 1 mM sodium pyruvate (Gibco). $CRC^+$ additionally required 10% ConA treated T cell supernatant. In vivo RNK-16 tumor cells were obtained from serial ascites passage in Fisher (F344) rats. Normal rat spleens and thymuses were aseptically removed and single-cell suspensions prepared in RPMl 1640 with 10% heat-inactivated FCS. Splenic mononuclear cells were harvested after centrifugation on Ficoll/Hypaque gradients at 300 g for 20 min. Rat A-LAK splenocytes were prepared as described previously (Vujanovic, N. L., et al. *J. Exp. Med.* 167:15–29 (1988)). Briefly, $10^8$ splenocytes in RPMI 1640, 10% FCS, were added to a 10 cc syringe containing 4 g of sterile nylon wool (1 h, 37° C.) to reduce contaminating B cells and monocytes. The nylon non-adherent splenocytes were collected and washed. These splenocytes and thymocytes were cultured in the absence or presence of 20 ng/ml phorbol myristate acetate (PMA) (Sigma) and 1000 U/ml recombinant human IL-2 (Kindly provided by Cetus Corp., Emeryville, Calif.) for 4 days. Thymocytes were harvested and spleen A-LAK cells were obtained by culturing the plastic-adherent (A) splenocytes in the conditioned medium (4 days) for a further 2 days (Vujanovic, N. L., et al. *J. Exp. Med.* 167:15–29 (1988)). Total cellular RNA from normal rat brain, liver and colon was extracted by homogenizing the tissues in 5M guanidine thiocyanate.

Total cytoplasmic RNA was purified from all cells by the method of Chomczynski, et al (Chomczynski, P., and Sacchi, N. *Anal. Biochem.* 162:156–159 (1987)). For Northern analysis, 25 µg RNA was subjected to electrophoresis on a 0.8% agarose formaldehyde gel, then transferred to Nytran (Schleicher and Schuell, Keene, N.H.). All blots were hybridized to $^{32}$P-labeled RNK-Met-1 cDNA and human γ-actin (Gunning, P., et al. *Mol. Cell. Biol.* 3:787–795 (1983)) cDNA as described previously (Thomas, P. S. *Methods Enzymol.* 100:255–266 (1983)). The blots were then exposed to Kodak X-OMAT AR film for 0–7 days at −70° C.

Human Met-ase. A cDNA clone encoding a human T cell and large granular lymphocyte (LGL)-specific serine protease was obtained by screening a phage λgt10 cDNA library from the human Lopez LGL leukemia with the rat RNK-Met-1 (Met-ase) cDNA clone. The Lopez cDNA phage library was constructed using the λgt10 vector and EcoRI cDNA inserts derived from human Lopez NK leukemia mRNA at the Slone Kettering Memorial Cancer Center (New York, N.Y.) by Dr. Joseph Trapani. The phage library was screened by plaque hybridization ($1\times10^6$) with random-primed rat RNK-Met-1 cDNA. All filter hybridizations were performed at 42° C. in the presence of 5×SSC containing 25% formamide; the filters were washed with 2×SSC at 55° C. The recombinant phages were plaque purified, isolated from overnight liquid cultures and phage DNA was purified, EcoRI digested and subcloned into the EcoRI site of the vector pBluescript $KS^+$. Sequencing was performed in both orientations using synthetic oligonucleotides, the dideoxy method and single stranded and double stranded templates. The entire final sequence was determined from both strands.

Results

Biochemical Purification of a Novel Serine Protease From the Granules of a Rat NK Leukemia.

Extracts of granules from the rat NK cells lines RNK-7 and RNK-16 have previously been reported to exhibit a number of protease activities including Tryptase, Chymase, Asp-ase, Met-ase, and Ser-ase activities when tested against a variety of synthetic substrates (Hudig, D., et al. *J. Immunol.* 147:1360–1368 (1991)). Whether these different enzymatic activities are due to distinct highly specific proteases or are the result of the broad substrate specificity of a more limited number of individual proteases is at present unclear. The biochemical purification to homogeneity of one of these proteases, RNKP-1, which exhibited an Asp-ase activity but appeared devoid of Met-ase activity also has been reported (Sayers, T. J., et al. *J. Immunol.* 148: 292–300 (1992)). A similar biochemical strategy was used herein in order to purify the Met-ase activity from the RNK granules.

Figure 1B:
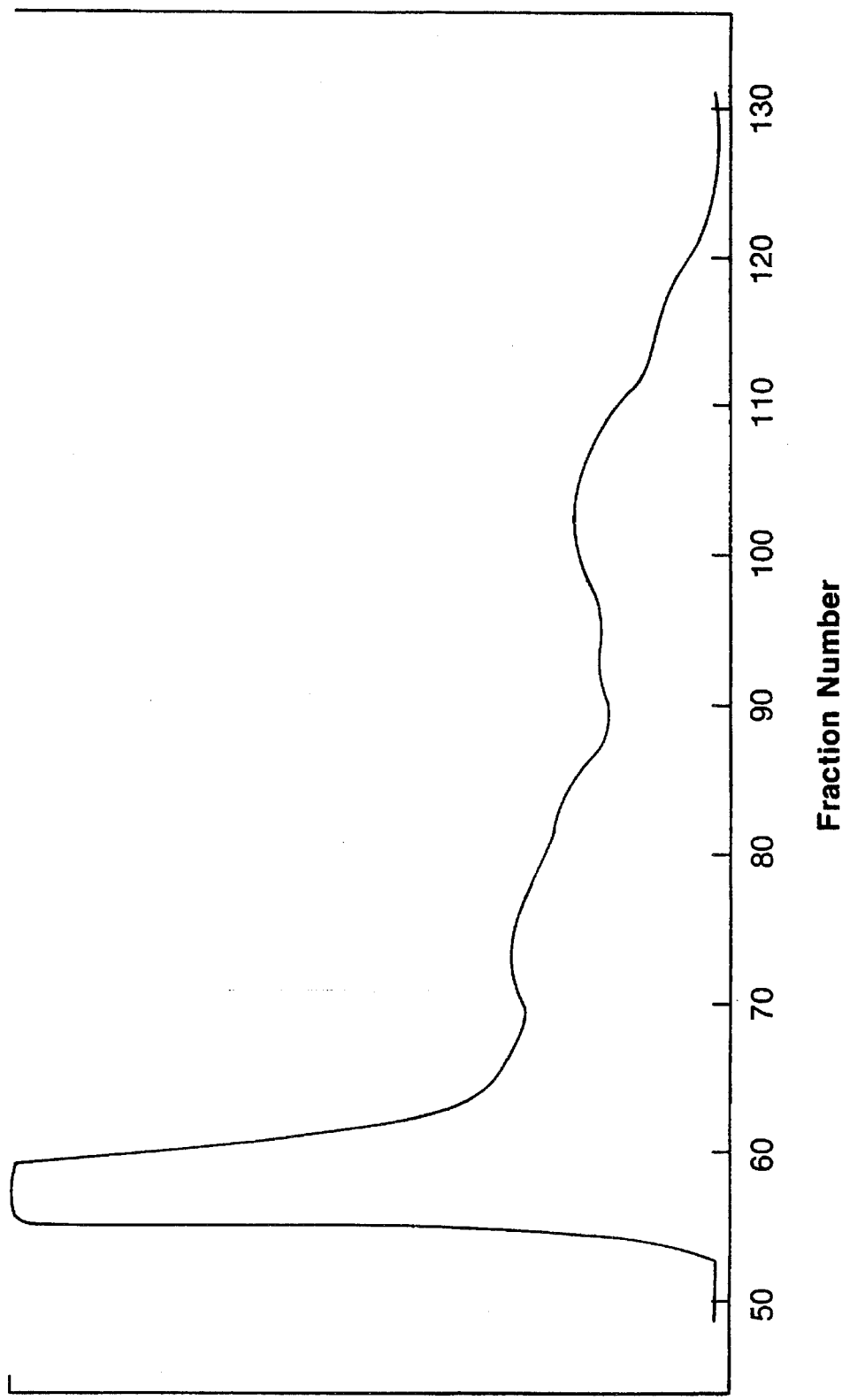

The granule constituents were first fractionated on an ACA 54 column and fractions were collected and tested for Met-ase, Tryptase (BLT-esterase) and cytolysin (PFP) activities as shown in FIGS. 1A and 1B. The cytolytic activity was located in one major peak around 60–70 kDA as would be expected. BLT-esterase activity was localized in two peaks, one at 60–70 kDA overlapping the cytolysin activity and another around 25–35 kDA. The bulk of the Met-ase activity was associated with a peak which exhibited a slightly higher molecular mass than the smaller BLT-esterase, although a high degree of overlap between these two activities occurred. Some Met-ase activity was observed in fractions containing proteins of 70–80 kDa. This activity, however, was not further investigated. In an attempt to purify the lower molecular mase Met-ase activity from the BLT-esterase activity, fractions 96–108 were pooled, concentrated and subjected to heparin-agarose affinity chromatography. As seen in Table 1, the vast majority of both the Met-ase and BLT-esterase activities bound to heparin and were eluted at a salt concentration of 0.65M NaCl. Although this step resulted in a substantial purification of both the Met-ase and BLT-esterase activities, the two activities could not be discriminated from each other using this procedure and thus reverse phase HPLC chromatography was employed.

Figure 2:
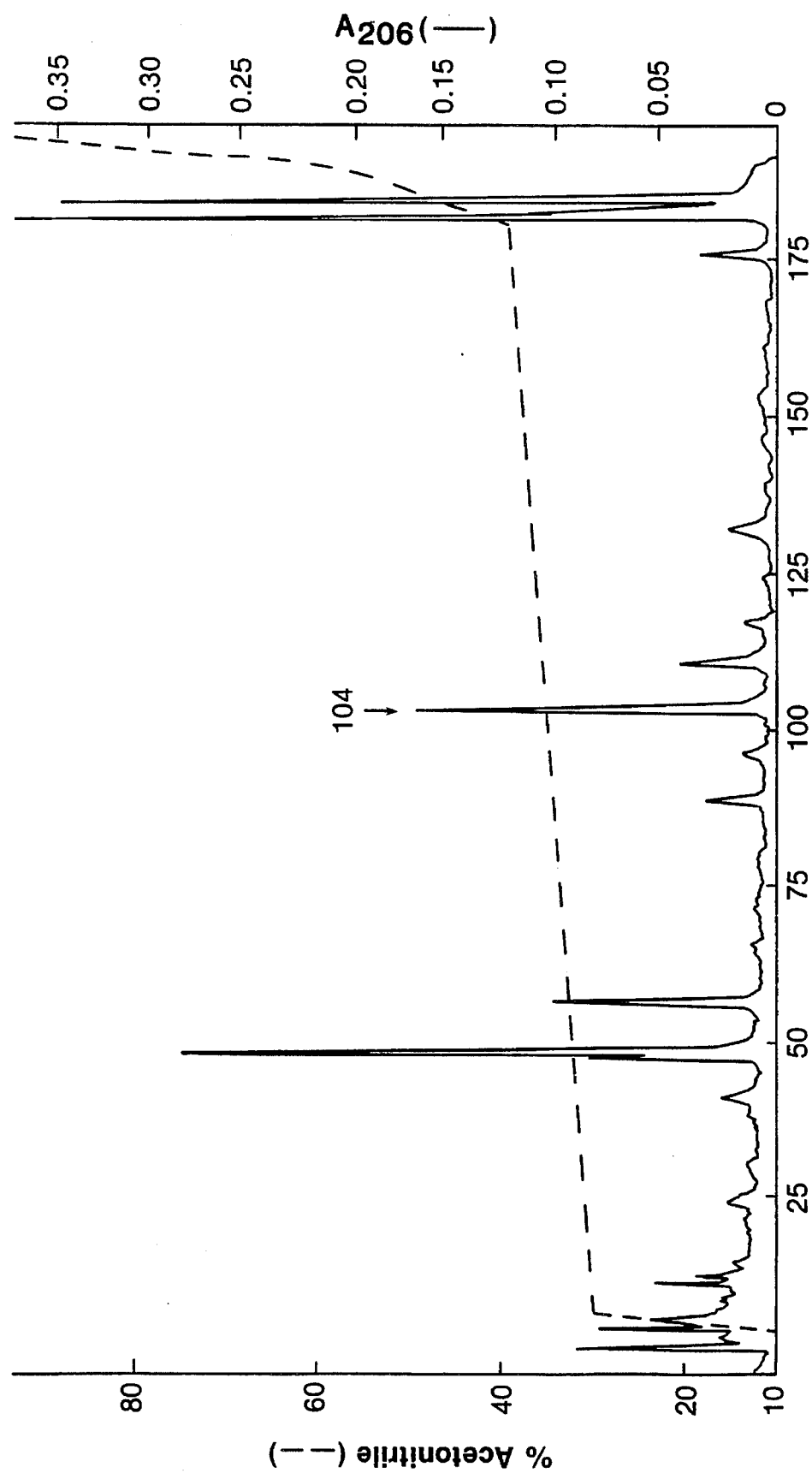
FIG. 2. Isolation of the Met-ase on reverse phase HPLC. For enzymatic analysis an aliquot of each fraction was lyophilized to dryness in the presence of 50µg of BSA, reconstituted in PBS and extensively dialysed against PBS. An aliquot of fraction 104 which contained most of the Met-ase activity was lyophilized to dryness and then sequenced using the Edman degradation procedure.

Fractionalization of HPLC chromatography using a very shallow gradient of acetonitrile (30–38%) resulted in the resolution of several protein peaks (FIG. 2). The bulk

TABLE 1

Heparin Agarose Affinity Chromatography of the Granule Metase

| Fraction[a] | [NaCl] (M) | Volume (ml) | [Protein] (μg/ml) | Metase[b] ($OD_{410}$ nm) | BLT-esterase[c] ($OD_{410}$ nm) |
|---|---|---|---|---|---|
| ACA pool 3 (input) | | 4.5 | 336 | 1.00 | 0.93 |
| Eluates[a] | 0.1 | 2 | 120 | 0.15 | 0.03 |
| | 0.3 | 2 | 10 | 0.04 | 0.03 |
| | 0.65 | 2 | 128 | 0.81 | 1.43 |
| | 1.0 | 2 | 168 | 0.10 | 0.06 |

[a]Eluates from the heparin agarose column were concentrated and dialyzed against PBS.
[b]A 10 μl aliquot was assayed for Met-ase activity and the $OD_{410}$ nm after 5 min is presented.
[c]A 10 μl aliquot was assayed for BLT-esterase activity and the $OD_{410}$ nm after 5 min. is presented.

of the Met-ase activity was associated with HPLC fraction 104 (Table 2), although activity was also detected in fractions 111–113. The BLT-esterase activity was found in fractions 49 and 56. In the chromatogram shown in FIG. 2, a clear separation of the BLT-esterase and the Asp-ase activities was not obtained since the majority of the Asp-ase activity was located in fraction 48 which also contained some BLT-esterase activity. However, the purification of the Asp-ase to complete homogeneity has been described (Sayers, T. J., et al. *J. Immunol.* 148: 292– 300 (1992)), and one such preparation was used for enzymatic analysis in Table 2. Analysis of the enzyme activities of these HPLC purified proteins against synthetic substrates demonstrated that Asp-ase, Tryptase (BLT-esterase), and Met-ase activities could easily be distinguished from each other whereas Asp-ase and Ser-ase activities co-eluted upon HPLC chromatography (Table 2). The purified Met-ase also had some activity against synthetic peptides containing leucine or norleucine in the P1 position, but no activity against Asp-ase, Tryptase, or Chymase substrates. The purification of the Met-ase to homogeneity from the granule extract resulted in a 29 fold increase in the specific activity (Table 3).

Figure 3A:
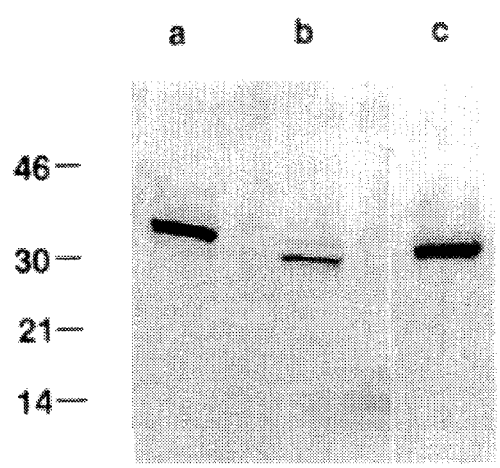
FIGS. 3A and 3B. PAGE of HPLC purified rat granule serine proteases under reducing (FIG. 3A) or non-reducing (FIG. 3B) conditions. Asp-ase (lane a), Tryptase (lane b) and Met-ase (lane c). The positions of the molecular mass standards 46, 30, 21 and 14 kDa are shown.
Figure 3B:
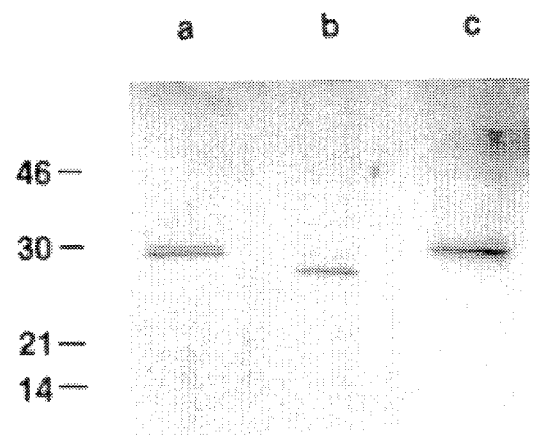

As expected, PAGE of the granule Met-ase, Asp-ase and BLT-esterase demonstrated that the proteins had a very similar molecular mass (FIGS. 3A and 3B). Under reducing conditions the apparent molecular mass of the Met-ase was 30 kDa in comparison to 32 kDa for the Asp-ase and 25 kDa for the BLT-esterase. Interestingly, the apparent molecular mass of both the Met-ase and the BLT-esterase remained the same under nonreducing conditions whereas the Asp-ase migrated at 29 kDa. The N-terminal amino acid sequence was determined for the Met-ase protein using the Edman degradation method. One unambiguous N-terminal sequence was found and it is underlined in FIGS. 4A and 4B. This sequence was not found in the database of the NCI Biomedical

TABLE 2

Substrate Activities of Rat Granzymes Purified by Reverse Phase HPLC Chromatography[a]

| | | Initial Rates (nM/s) | | |
|---|---|---|---|---|
| Substrates | [S] (μM) | Asp—ase[b] | Tryptase[c] | Met—ase[d] |
| Z—Arg—SBzl | 106 | 0 | 22.7 93.4[e] | 0 |
| Boc—Ala—Ala—Asp—SBzl | 116 | 12.6 44.6[e] | 0 | 0 |
| Boc—Ala—Ala—Met—SBzl | 116 | 0 | 0 | 4.2 13.7[e] |
| Suc—Ala—Ala—Met—SBzl | 114 | | | 10.1[e] |
| Boc—Ala—Ala—Leu—SBzl | 112 | | | 2.9 |
| Boc—Ala—Ala—Nle—SBzl | 100 | | | 3.9 15.2[e] |
| Boc—Ala—Ala—Ser—SBzl | 133 | 1.3 6.7[e] | 0.4 | 0 |
| Suc—Phe—Leu—Phe—SBzl | 114 | 0 | 0 | 0 |

[a]Initial rates were measured in 0.1 M Hepes, 0.01 M $CaCl_2$, pH 7.5 buffer, 8% $Me_2SO$ and 25° C. in the presence of 4,4'-dithiodipyridine (0.34 mM). 10 μl of enzyme solution was added to the assay mixture.
[b]Asp-ase purified by HPLC as previously described (Sayers, T. J., et al. J. Immunol. 148: 292–300 (1992)).
[c]HPLC fraction 56.
[d]HPLC fraction 104.
[e]25 μl of enzyme solution was added.

TABLE 3

Yield of the Metase on Purification from PNK Granules

| Fraction | Volume (ml) | Concn. (μg/ml) | Protein in assay (μg) | Rate (nM/sec) | Specific Activity (nM/sec/μg protein) | Total (nM/sec) |
|---|---|---|---|---|---|---|
| Granules (salt extract) | 14 | 250 | 10 | 61 | 6.1 | 21,350 |
| ACA 54 (pool) | 4.5 | 336 | 3.4 | 57 | 16.9 | 25,552 |
| Heparin-Ag Affinity (0.65 M NaCl eluate) | 2.0 | 128 | 1.3 | 74 | 58.0 | 14,848 |
| HPLC Peak | 2.0 | 9 | 0.1 | 17 | 156.0 | 2,807 |

Supercomputing Center indicating that the rat Met-ase is a novel protein, which is designated RNK-Met-1.

Generation of RNK-Met-1 cDNA Probe Using the N-terminal Amino Acid Sequence Determination.

Two oligonucleotide primers were prepared to PCR amplify a RNK-Met-1 cDNA probe from RNK-16 total cellular RNA. The first of these (5'–3' primer) (SEQ ID NO:5 and SEQ ID NO:6) was a degenerate 41 mer coding for a 12 amino acid (SEQ ID NO:7) unique region in the N-terminus of the RNK-Met-1 protein. The second (3'–5' primer) (SEQ ID NO:8) was a 21 mer based on an Asp-Ser- Gly-Gly-Pro (SEQ ID NO:9) amino acid sequence around the active-site Ser that is completely conserved in the majority of reported SP proteins. This sequence is located 183–187 amino acids downstream from the N-terminus of the mature SP protein and thus if the RNK-Met-1 gene also encoded for a similar or identical stretch of amino acids, a PCR product of approximately 540 bp would be predicted. Indeed, stringent PCR amplification of total cellular RNA from rat RNK-16, yielded a single 534 bp product. No PCR products were obtained in the absence of either primer or when using total cellular RNA from rat N1S1 hepatoma cells as the template.

Nucleotide and Predicted Amino Acid Sequence RNK-Met-1 Indicate a Unique Serine-Dependent Protease.

The PCR product obtained was subcloned and used to screen a RNK-16 cDNA library to isolate a full length clone (FIGS. 4A and 4B). The insert of 867 bp contained a 774 bp open reading frame with 93 bp of 3' non coding region. The N-terminus of the mature SP protein (+1) and the TGA stop codon are indicated in FIGS. 4A and 4B. The RNK-Met-1 cDNA encodes a putative mature protein with 238 amino acids. The predicted m.w. for the unglycosylated protein is 26,014, which compared favorably with the observed m.w. on reduced and non-reduced (~30,000) SDS-PAGE gels (FIGS. 3A and 3B). The predicted isoelectric point of RNK-Met-1 is 10.38 confirming its highly basic nature. The mature protein, as determined by amino acid sequencing, begins at +1 with the conserved sequence Ile-Ile-Gly-Gly (SEQ ID NO:10) found in activated SP. The amino acid sequence of the predicted protein demonstrates sequence similarities to previously published CTL SP (Table 4). RNK-Met-1 demonstrated approximately similar identity (<45%) with other SP from human, mouse and rat species, including granzyme (SP) A. This suggests that RNK-Met-1 is just as distinct as SP A from other SP. Up to 55.5% identity between SP and RNK-Met-1 was observed at the nucleotide level (data not shown). The three key amino acids representing the catalytic triad of serine proteases are the His at position 41, Asp at position 87 and Ser at position 184 (FIGS. 4A and 4B). The sequence Val-Leu-Thr-Ala-Ala-His-Cys (SEQ ID NO:11) around the His (position 41) and the sequence Gly-Asp-Ser-Gly-Gly-Pro (SEQ ID NO:12) around the active site Ser of SP are highly conserved. The mature RNK Met-1 protein contains 8 cysteine residues, 6 of which are conserved in all SP (positions 26, 42, 122, 153, 169, and 190). These conserved cysteines are expected to form three disulfide bonds (26-42, 122-153, 169-190) while the other two cysteines of RNK-Met-1 (position 180 and 206) may be analogous to the disulfide bond linking residues (position 191 and 220) in α-chymotrypsin which bridge the active-site serine.

RNK-Met-1 has several features which distinguish it from other known members of the SP family. The predicted first 20 amino acids of the RNK-Met-1 polypeptide chain are part of the hydrophobic SP signal peptide. However, the signal sequence is distinct from those derived according to the algorithm developed by von Heijne (von Heijne, G. *Nucleic Acids Res.* 14:4683–4690 (1986)).

The typical acidic SP propeptide at the amino terminus is not present in RNK-Met-1 but rather the leader peptide appears to be an exception in that it ends with a Glu residue. The combination of amino acid residues that are thought to determine the specificity of the substrate binding pocket (−6, +15, +16, +17, +28 relative to the active-site serine) are quite unique in RNK-Met-1. The

TABLE 4

Similarity of RNK-Met-1 protein with related serine proteases[a]

| Protein | Species | Sequence position units | % Identity |
|---|---|---|---|
| Granzyme B | Human | 1-247 | 41.7 |
| Adipsin | Human | 1-228 | 40.3 |
| RNKP-1 | Rat | 1-248 | 39.9 |
| Cathepsin G | Human | 1-255 | 39.4 |
| Granzyme D | Mouse | 1-252 | 38.1 |
| CCP1 | Mouse | 1-247 | 37.6 |
| Adipsin | Mouse | 1-258 | 37.0 |
| Granzyme A | Mouse | 1-262 | 36.7 |
| Hepatocyte growth factor | Rat | 451-728 | 35.3 |

[a]The Gap (Genetics Computer Group) was used for amino acid sequence comparison following a PEPTIDESORT of the predicted RNK-Met-1 sequence against NBRF-PIR, Swissprot and Translation of Genbank.

(−6) $Ala^{178}$ of RNK-Met-1 is uncharged and therefore suggests a chymotrypsin-like activity. However, the $Ser^{200}$-Phe-Ser stretch (corresponding to +15 to +17) is clearly distinct from that found in any chymotrypsin-like or trypsin-like SP described thus far. Furthermore, RNK-Met-1 is the only SP known to have a Thr +28/29 residues C-terminal to the active-site serine. Two potential N-glycosylation sites $Asn^{154}$-Asn-Ser and $Asn^{205}$-Cys-Thr (Asn-X-Ser/Thr) are present, the former with no obvious counterpart amongst other known SP.

Expression of rat RNK-Met-1 mRNA.

Figure 5A:
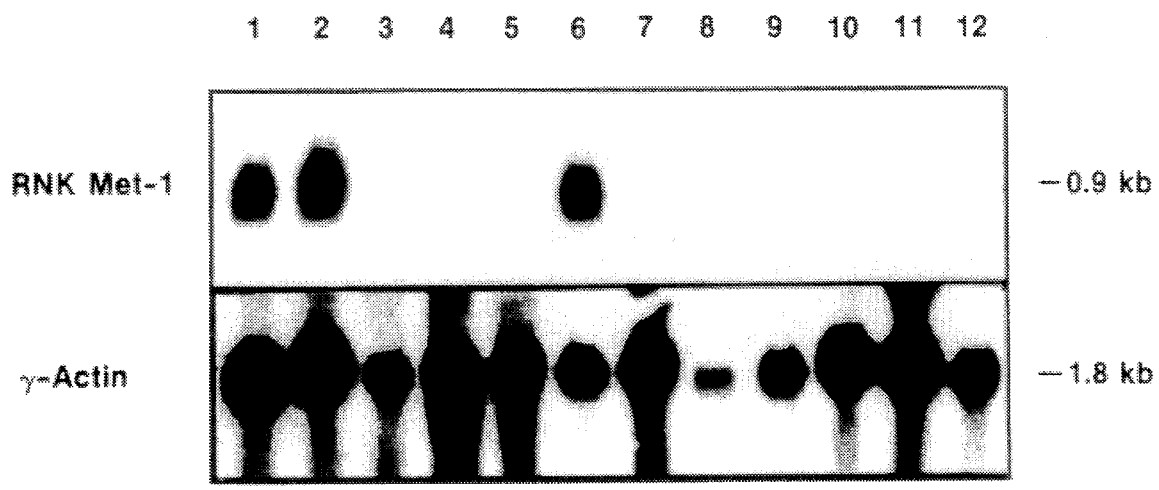
FIGS. 5A and 5B. Northern blot analysis of RNK-Met-1 expression. Total cellular RNA was isolated from the following tissues and cell lines (as described in the Materials and Methods)
Figure 5B:
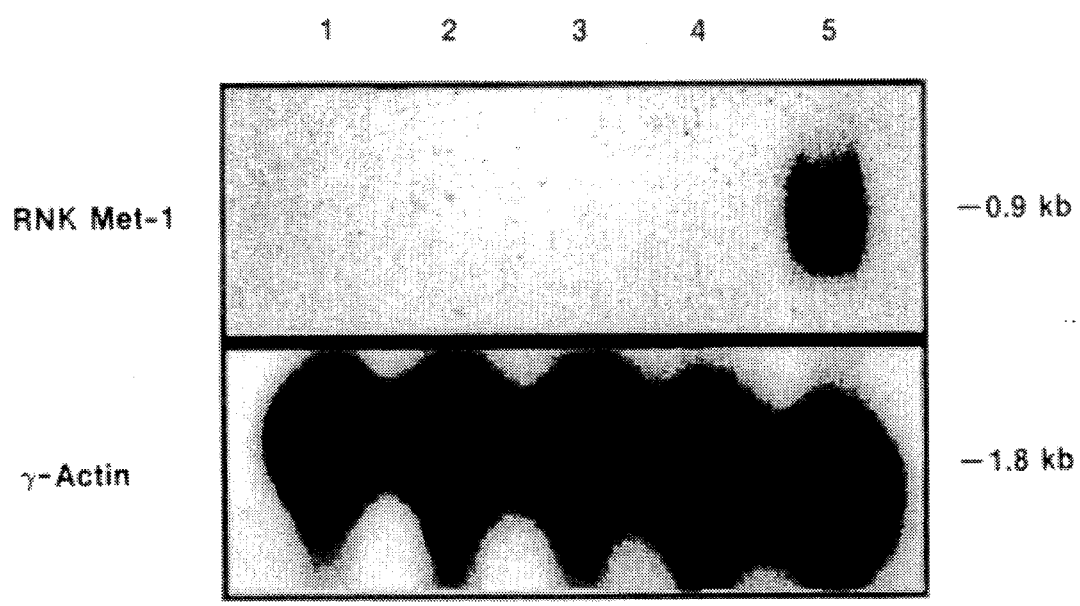

Northern analysis detected an approximately 0.9 kb mRNA in total cellular RNA from in vitro and in vivo variants of RNK-16 (FIG. 5A). Equivalent levels of RNK-Met-1 mRNA were also detected in total cellular RNA from rat spleen cells that had been passed over nylon wool, cultured in IL-2 (1000 U/ml) and PMA (20 ng/ml) for 4 days, selected for plastic adherence and further cultured in the conditioned medium for another 2 days (classical rat A-LAK cells (Vujanovic, N. L., et al. *J. Exp. Med.* 167:15–29 (1988)) (FIG. 5B). By comparison, RNK-Met-1 mRNA could not be detected in total cellular RNA from unstimulated rat liver, colon, brain, spleen or thymus (FIG. 5A and B). In addition, rat splenocytes that were passed over nylon wool and cultured in media did not express detectable RNK-Met-1, nor did thymocytes cultured in IL-2 and PMA (as above). No cross reactivity of the RNK-Met-1 cDNA probe with total cellular RNA from human or murine NK, CTL and other cell lines was detected (FIG. 5A). Expression of γ-actin mRNA in all the samples examined indicated that the total cellular RNA was intact.

Human Met-ase. Nucleotide sequencing of the cDNA clones reveals the Met-ase to be a unique member of the lymphocyte SP family. From the human nucleotide sequence, the amino acid sequence was deduced. The deduced human amino acid sequence has 66.4% identity with the rat amino acid sequence (See Table 5).

TABLE 5

| HUMAN | IIGGREVIPH | SRPYMASLQR | NGSHLCGGVL | 30 |
|---|---|---|---|---|
| RAT | ......AV.. | .....V... N | TK..M..... | 30 |

TABLE 5-continued

| | | | | |
|---|---|---|---|---|
| HUMAN | VHPKWVLTAA | HCLAQRMAQL | RLVLGLHTLD | 60 |
| RAT | W.Q....... | ...SEPIQ.. | K..F...S.H | 60 |
| HUMAN | ---SPGLTFHIKA | AIQHPRYKPV | PALVFDIALL | 90 |
| RAT | DPQD.....Y..Q | ..K..G.NLK | --YEN..... | 91 |
| HUMAN | QLDGKVKPSR | TIRPLALPSK | H-QVVAAGTRC | 120 |
| RAT | K...R....K | NVK.....R. | PRDKP.E.S.. | 122 |
| HUMAN | SMAGWGLTHQ | GGGLSRVLAE | LDLQVLDTRM | 150 |
| RAT | T....I... | R.Q.AKS.Q. | ...RL..... | 152 |
| HUMAN | CNNSRFWNGS | LSPSMVCIAA | DSLDQAPCKG | 180 |
| RAT | .........V | TD..L..K. | GA.G...... | 182 |
| HUMAN | DSGGPLVCGK | GRVLAGVLSF | SSRVCTDIFK | 210 |
| | ......... | K.D-.I... | ..KN...... | 211 |
| HUMAN | PPVATAVAPY | VSWIRKVTGR | SA | 232 |
| RAT | .T........ | S......I.. | WSPQPT | 238 |

81/241 differences, SO% IDENTITY = 66.4% (INC. GAPS)
7 CYS RESIDUES AND CATALYTIC TRIAD (HDS) ALL CONSERVED

Discussion

Despite the large number of murine SP characterized, only one gene encoding a rat counterpart (RNKP1, Asp-ase, SP B) and three genes encoding human counterparts (SP A, B and C) have been described. Hereinabove, a novel rat SP, RNK-Met-1, has been purified to homogeneity from the granules of a rat RNK-16 LGL leukemia in an enzymatically active form by a three step procedure. It was significant to maintain the enzymatic activity of RNK-Met-1 since leukocyte granules have been shown to contain SP-like proteins devoid of proteolytic activity (Wilde, C. G., et al. *J. Biol. Chem.* 265:2038–2041 (1990)). Three SP activities (Asp-ase, Tryptase and Met-ase) have been purified in an enzymatically active form. Previously, human and murine SP have been examined using the same set of thiobenzylester substrates used to measure RNK-Met-1 activity (Odake, S., et al. *Biochemistry* 30:2217–2227 (1991)). SPA hydrolyzed Arg- or Lys-containing substrates most effectively, but also hydrolyzed substrates such as Suc-Phe-Leu-Phe-SBzl and Suc-Ala-Ala-Pro-Phe-SBzl at much slower rates. SP D, E and F demonstrated minor activity toward Arg- or Lys-containing substrates and SP F also had activity toward Suc-Phe-Leu-Phe-SBzl. SP C did not hydrolyze any thioester substrate. The cloned RNK-Met-1 cDNA predicts a 238 amino acid mature protein with several structural features consistent with all SP isolated to date. The characteristic N-terminal sequence Ile-Ile-Gly-Gly (SEQ ID NO:10) was present in RNK-Met-1. In addition, the His, Asp and Ser residues that make up the active-site Ser charge relay system were found in RNK-Met-1 at homologous positions flanked by well-conserved peptide segments present in all SP family members. Six cysteine residues (of a total of 8) were conserved in homologous positions and are expected to form three internal disulfide bonds. The other two cysteine residues of RNK-Met-1 (position 180 and 206) may be analogous to the disulfide bond linking residues 191 and 220 in α-chymotrypsin, which bridge the active site serine (Le Trong, J., et al. *Proc. Natl. Acad. Sci. USA* 84:364–367 (1987); Le Trong, J., et al. *Biochemistry* 26:6988–6994 (1987)). Significantly, all of the chymotrypsin-like SP of lymphocytes described thus far lack this disulfide bond, while the trypsin like SP A has 9 cysteines including those at positions 180 and 206 (Gershenfeld, H. K., et al. *Proc. Nat'l Acad. Sci. USA* 85:1184–1185 (1988)).

RNK-Met-1 has other features distinguishing it from the chymotrypsin-like SP and likening it to trypsin-like SP A and kallikrein gene family (Mason, A. J., et al. *Nature* 303:300–307 (1983)). The signal peptides of the chymotrypsin-like SP are followed by a two- or four-residue propeptide (activation peptide) ending in a Glu (Jenne, D., et al. *Proc. Natl. Acad. Sci. USA* 85:4814–4818 (1988)). However the propeptides of SPA and kallikrein (mGK-1) end with a basic residue, Arg (Gershenfeld, H. K., et al. *Proc. Nat'l Acad. Sci. USA* 85:1184–1185 (1988); Mason, A. J., et al. *Nature* 303:300–307 (1983)); and the putative propeptide of RNK-Met-1 is at least 20 residues long and also ends with a basic residue, Gln. Interestingly, RNK-Met-1 also displays characteristics that differ from those documented in trypsin-like SP. The amino acid residue located (–6) positions amino-terminal to the active-site serine forms the bottom of the $S_1$ substrate binding pocket and this determines the substrate specificity in the $P_1$ position of a substrate (Kraut, J. *Annu. Rev. Biochem.* 46:331–358 (1977); Bode, W., et al. *Biochemistry* 28:1951–1963 (1989)). Similar to: SP D, E and H (Thr); SP B and C, Cathepsin G and rat mast cell protease (RMCP) II (Ala); and SP F and α-chymotrypsin (Ser), the $Ala^{178}$ (–6 from $Ser^{184}$) of RNK-Met-1 is an uncharged residue and therefore suggests a chymotrypsin-like activity. By contrast, the trypsin-like SP A which cleaves after Lys or Arg residues contains the negatively charged Asp six residues N-terminal to its active-site serine. The low polarity of $Ala^{178}$ in RNK-Met-1 indicates a preference for a hydrophobic amino acid at the $P_1$ position in the substrate and methionine fits this description. However, residues at positions +15 to +17 and +28 relative to the active-site serine are thought to determine the specificity of the substrate binding pocket (Kraut, J. *Annu. Rev. Biochem,* 46:331–358 (1977); Bode, W., et al. *Biochemistry* 28:1951–1963 (1989)). Insertion of an additional residue between the active-site serine and this 3 amino acid stretch positions these residues +16 to +18 and +29 C terminal in RNK-Met-1. When the corresponding residues of RNK-Met-1 in these positions are compared to those of other SP, amino acid replacements are observed, suggesting distinct substrate specificity due to the altered shape and size of the substrate binding pocket. The Ser-Phe-Ser amino acid stretch in RNK-Met-1 is distinct from α-chymotrypsin (Ser-Trp-Gly) and SPA (Ser-Phe-Gly) and those SP containing a Tyr 16 positions C-terminal to the active-site serine (Ser-Try-Gln in SP B, C and H, RMCPI and II, Cathepsin G and human leukocyte protease; Ala-Tyr-Ala in SP D and E; and Thr-Tyr-Gly in SP F). RNK-Met-1 is the only SP described thus far with a Thr +28/29 residues C-terminal to the active-site serine.

The putative N-glycosylation sites Asn-Asn-Ser (positions 154–156) and Asn-Cys-Thr (positions 205–207) in RNK-Met-1 are distinct from putative N-glycosylation sites in SP B (positions 65, 98), SP H (position 65, 98, 175) and Cathepsin G (position 65). The $Asn^{205}$-Cys-Thr peptide of RNK-Met-1 is similar to one of 3, 4 and 5 sites present in SP F, E and D respectively. However, the $Cys^{206}$ residue may also putatively be disulfide bonded to $Cys^{180}$ and therefore the likelihood of N-glycosylation at this site might be questioned. Differences in glycosylation may influence the specificity of substrate binding (Salvensen, G., et al. *Biochemistry* 26:2289–2293 (1987)) and may result in functional heterogeneity when this site is not constantly used for glycosylation. Additionally, the amount of negatively charged N-linked carbohydrate influences the net charge of the SP and may affect the affinity for proteoglycans and their dissociation rates after secretion. The presence and functional role of N-glycosylation in RNK-Met-1 remain to be determined.

Clearly, RNK-Met-1 is expressed in activated rat A-LAK splenocytes. Whether RNK-Met-1 is also expressed in non-cytolytic cells and non-lymphoid lineages is not known. Although, RNK-Met-1 has only been detected in rat LGL, Met-ase activities have been described for granule preparations from human CTL and murine NK cells (Odake, S., et al. *Biochemistry* 30:2217–2227 (1991); T. J. Sayers, unpublished data). Homologous mRNAs were not detected in human LGL- or murine CTL-cell lines by Northern analysis. However, Southern analysis of human and murine genomic DNA would suggest that RNK-Met-1- like genes do exist in these species (data not shown). Evidently, with few exceptions, murine SP gene expression is restricted to T cells and their thymic precursors and NK cells (Garcia-Sanz, J. A., et al. *J. Immunol.* 145:3111–3118 (1990)).

All publications mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A purified and isolated nucleic acid molecule encoding a serine protease having the amino acid sequence selected from the group consisting of: (a) the amino acid sequence contained in FIGS. 4A and 4B (SEQ ID NO:2); and (b) the amino acid sequence contained in FIGS. 6A and 6B (SEQ ID NO: 4).

2. The nucleic acid molecule of claim 1 encoding the amino acid sequence contained in FIGS. 4A and 4B (SEQ ID NO:2).

3. The nucleic acid molecule of claim 1, encoding the amino acid sequence contained in FIGS. 6A and 6B (SEQ ID NO:4).

4. The nucleic acid molecule of claim 1, having the DNA sequence contained in FIGS. 4A and 4B (SEQ ID NO:1).

5. The nucleic acid molecule of claim 1, having the DNA sequence contained in FIGS. 6A and 6B (SEQ ID NO:3).

6. A vector comprising the nucleic acid molecule of claim 1.

7. A vector comprising the nucleic acid molecule of claim 2.

8. A vector comprising the nucleic acid molecule of claim 3.

9. A vector comprising the nucleic acid molecule of claim 4.

10. A vector comprising the nucleic acid molecule of claim 5.

11. A prokaryotic or eukaryotic host cell stably transformed or transfected with the vector of claim 6.

12. A prokaryotic or eukaryotic host cell stably transformed or transfected with the vector of claim 7.

13. A prokaryotic or eukaryotic host cell stably transformed or transfected with the vector of claim 8.

14. A prokaryotic or eukaryotic host cell stably transformed or transfected with the vector of claim 9.

15. A prokaryotic or eukaryotic host cell stably transformed or transfected with the vector of claim 10.

16. A method for detecting nucleic acid encoding Met-ase in a sample which comprises contacting nucleic acid from the sample with the nucleic acid molecule of claim 1 under conditions permitting hybridization to occur, and determining that hybridization has occurred, thereby detecting nucleic acid encoding Met-ase in the sample.

17. A method for detecting nucleic acid encoding Met-ase in a sample which comprises contacting nucleic acid from the sample with the nucleic acid molecule of claim 2 under conditions permitting hybridization to occur, and determining that hybridization has occurred, thereby detecting nucleic acid encoding Met-ase in the sample.

18. A method for detecting nucleic acid encoding Met-ase in a sample which comprises contacting nucleic acid from the sample with the nucleic acid molecule of claim 3 under conditions permitting hybridization to occur, and determining that hybridization has occurred, thereby detecting nucleic acid encoding Met-ase in the sample.

19. A method for detecting nucleic acid encoding Met-ase in a sample which comprises contacting nucleic acid from the sample with the nucleic acid molecule of claim 4 under conditions permitting hybridization to occur, and determining that hybridization has occurred, thereby detecting nucleic acid encoding Met-ase in the sample.

20. A method for detecting nucleic acid encoding Met-ase in a sample which comprises contacting nucleic acid from the sample with the nucleic acid molecule of claim 5 under conditions permitting hybridization to occur, and determining that hybridization has occurred, thereby detecting nucleic acid encoding Met-ase in the sample.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 867
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: RAT
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE: CYTOLYTIC GRANULE
        ( H ) CELL LINE: RNK-16 LGL
        ( I ) ORGANELLE:

( x i ) SEQUENCE DESCRIPTION:SEQ ID NO:1:

```
CTG  CTG  CTC  CTG  CTG  GCC  CTG  AAA  ACA  CTG  TGG  GCA  GTA          39
Leu  Leu  Leu  Leu  Leu  Ala  Leu  Lys  Thr  Leu  Trp  Ala  Val
-20                      -15                      -10

GGC  AAC  AGA  TTT  GAG  GCC  CAG  ATC  ATT  GGG  GGT  CGA  GAG          78
Gly  Asn  Arg  Phe  Glu  Ala  Gln  Ile  Ile  Gly  Gly  Arg  Glu
          -5                        1                   5

GCA  GTC  CCG  CAC  TCC  CGC  CCA  TAC  ATG  GTC  TCG  CTA  CAG         117
Ala  Val  Pro  His  Ser  Arg  Pro  Tyr  Met  Val  Ser  Leu  Gln
               10                        15

AAT  ACC  AAG  TCC  CAC  ATG  TGT  GGG  GGA  GTC  CTC  GTG  CAT         156
Asn  Thr  Lys  Ser  His  Met  Cys  Gly  Gly  Val  Leu  Val  His
20                        25                   30

CAG  AAG  TGG  GTG  TTG  ACC  GCT  GCC  CAC  TGC  CTG  TCT  GAA         195
Gln  Lys  Trp  Val  Leu  Thr  Ala  Ala  His  Cys  Leu  Ser  Glu
```

|  |  |  |  |  |  |  |  |  |  |  |  |  |
|---|---|---|---|---|---|---|---|---|---|---|---|---|
|  | 35 |  |  |  |  | 40 |  |  |  |  | 45 |  |
| CCG | CTA | CAG | CAG | CTG | AAG | CTG | GTG | TTC | GGC | CTG | CAC | AGC | 234
| Pro | Leu | Gln | Gln | Leu | Lys | Leu | Val | Phe | Gly | Leu | His | Ser |
|  |  |  |  | 50 |  |  |  |  | 55 |  |  |  |
| CTT | CAT | GAT | CCC | CAA | GAT | CCT | GGC | CTT | ACC | TTC | TAC | ATC | 273
| Leu | His | Asp | Pro | Gln | Asp | Pro | Gly | Leu | Thr | Phe | Tyr | Ile |
|  |  | 60 |  |  |  | 65 |  |  |  |  | 70 |  |
| AAG | CAA | GCC | ATT | AAA | CAC | CCT | GGC | TAC | AAC | CTC | AAA | TAC | 312
| Lys | Gln | Ala | Ile | Lys | His | Pro | Gly | Tyr | Asn | Leu | Lys | Tyr |
|  |  |  | 75 |  |  |  |  | 80 |  |  |  |  |
| GAG | AAC | GAC | CTG | GCC | CTG | CTT | AAG | CTG | GAT | GGA | CGG | GTG | 351
| Glu | Asn | Asp | Leu | Ala | Leu | Leu | Lys | Leu | Asp | Gly | Arg | Val |
| 85 |  |  |  |  | 90 |  |  |  |  | 95 |  |  |
| AAG | CCC | AGC | AAG | AAT | GTC | AAA | CCA | CTG | GCT | CTG | CCA | AGA | 390
| Lys | Pro | Ser | Lys | Asn | Val | Lys | Pro | Leu | Ala | Leu | Pro | Arg |
|  |  | 100 |  |  |  |  | 105 |  |  |  |  | 110 |
| AAG | CCC | CGA | GAC | AAG | CCT | GCA | GAA | GGC | TCC | CGG | TGT | AGC | 429
| Lys | Pro | Arg | Asp | Lys | Pro | Ala | Glu | Gly | Ser | Arg | Cys | Ser |
|  |  |  | 115 |  |  |  |  | 120 |  |  |  |  |
| ACG | GCT | GGA | TGG | GGT | ATA | ACC | CAC | CAG | AGG | GGA | CAG | CTA | 468
| Thr | Ala | Gly | Trp | Gly | Ile | Thr | His | Gln | Arg | Gly | Gln | Leu |
|  | 125 |  |  |  |  | 130 |  |  |  |  | 135 |  |
| GCC | AAG | TCC | CTG | CAG | GAG | CTC | GAC | CTG | CGT | CTT | CTG | GAC | 507
| Ala | Lys | Ser | Leu | Gln | Glu | Leu | Asp | Leu | Arg | Leu | Leu | Asp |
|  |  |  | 140 |  |  |  |  | 145 |  |  |  |  |
| ACC | CGG | ATG | TGT | AAC | AAC | AGC | CGC | TTC | TGG | AAC | GGT | GTC | 546
| Thr | Arg | Met | Cys | Asn | Asn | Ser | Arg | Phe | Trp | Asn | Gly | Val |
| 150 |  |  |  |  | 155 |  |  |  |  | 160 |  |  |
| CTC | ACG | GAC | AGC | ATG | CTG | TGC | TTA | AAG | GCT | GGG | GCC | AAG | 585
| Leu | Thr | Asp | Ser | Met | Leu | Cys | Leu | Lys | Ala | Gly | Ala | Lys |
|  |  | 165 |  |  |  |  | 170 |  |  |  |  | 175 |
| GGC | CAA | GCT | CCT | TGC | AAG | GGT | GAC | TCT | GGA | GGG | CCC | CTG | 624
| Gly | Gln | Ala | Pro | Cys | Lys | Gly | Asp | Ser | Gly | Gly | Pro | Leu |
|  |  |  |  | 180 |  |  |  |  | 185 |  |  |  |
| GTG | TGT | GGC | AAA | GGC | AAG | GTG | GAT | GGG | ATC | CTG | TCT | TTC | 663
| Val | Cys | Gly | Lys | Gly | Lys | Val | Asp | Gly | Ile | Leu | Ser | Phe |
|  | 190 |  |  |  |  | 195 |  |  |  |  | 200 |  |
| AGC | TCC | AAA | AAC | TGC | ACA | GAC | ATC | TTC | AAG | CCC | ACC | GTG | 702
| Ser | Ser | Lys | Asn | Cys | Thr | Asp | Ile | Phe | Lys | Pro | Thr | Val |
|  |  |  | 205 |  |  |  |  | 210 |  |  |  |  |
| GCC | ACT | GCT | GTA | GCC | CCC | TAC | AGC | TCC | TGG | ATC | AGG | AAG | 741
| Ala | Thr | Ala | Val | Ala | Pro | Tyr | Ser | Ser | Trp | Ile | Arg | Lys |
| 215 |  |  |  |  | 220 |  |  |  |  | 225 |  |  |
| GTC | ATT | GGT | CGC | TGG | TCA | CCC | CAG | CCT | CTG | ACC |  |  | 774
| Val | Ile | Gly | Arg | Trp | Ser | Pro | Gln | Pro | Leu | Thr |  |  |
|  |  | 230 |  |  |  |  | 235 |  |  |  |  |  |

| TGATGTCCCA | AACTATCTGG | GACATCATTC | TTGATGTCTG | GGGCTGGGAA | 824 |
| GGGACTAGGT | GTGCCTCTGG | GGATCAATAA | ATCCTGATAT | ATC | 867 |

( 2 ) INFORMATION FOR SEQ ID NO:2:

( i ) SEQUENCE CHARACTERISTICS:
        ( A ) LENGTH: 258
        ( B ) TYPE: AMINO ACID
        ( D ) TOPOLOGY: UNKNOWN ( i i ) MOLECULE TYPE:
        ( A ) DESCRIPTION: PROTEIN ( i i i ) HYPOTHETICAL: NO ( v i ) ORIGINAL SOURCE:

(A) ORGANISM: RAT
(B) STRAIN:
(C) INDIVIDUAL ISOLATE:
(D) DEVELOPMENTAL STAGE:
(E) HAPLOTYPE:
(F) TISSUE TYPE:
(G) CELL TYPE: CYTOLYTIC GRANULE
(H) CELL LINE: RNK-16 LGL
(I) ORGANELLE:

(xi) SEQUENCE DESCRIPTION:SEQ ID NO:2:

```
Leu  Leu  Leu  Leu  Leu  Ala  Leu  Lys  Thr  Leu  Trp  Ala  Val  Gly  Asn  Arg
-20            -15                      -10                           -5

Phe  Glu  Ala  Gln  Ile  Ile  Gly  Gly  Arg  Glu  Ala  Val  Pro  His  Ser  Arg
 1                                  5                          10

Pro  Tyr  Met  Val  Ser  Leu  Gln  Asn  Thr  Lys  Ser  His  Met  Cys  Gly  Gly
          15                  20                      25

Val  Leu  Val  His  Gln  Lys  Trp  Val  Leu  Thr  Ala  Ala  His  Cys  Leu  Ser
          30              35                      40

Glu  Pro  Leu  Gln  Gln  Leu  Lys  Leu  Val  Phe  Gly  Leu  His  Ser  Leu  His
 45                       50                  55                          60

Asp  Pro  Gln  Asp  Pro  Gly  Leu  Thr  Phe  Tyr  Ile  Lys  Gln  Ala  Ile  Lys
               65                       70                          75

His  Pro  Gly  Tyr  Asn  Leu  Lys  Tyr  Glu  Asn  Asp  Leu  Ala  Leu  Leu  Lys
               80                  85                          90

Leu  Asp  Gly  Arg  Val  Lys  Pro  Ser  Lys  Asn  Val  Lys  Pro  Leu  Ala  Leu
          95                  100                     105

Pro  Arg  Lys  Pro  Arg  Asp  Lys  Pro  Ala  Glu  Gly  Ser  Arg  Cys  Ser  Thr
     110                  115                     120

Ala  Gly  Trp  Gly  Ile  Thr  His  Gln  Arg  Gly  Gln  Leu  Ala  Lys  Ser  Leu
125                     130                     135                         140

Gln  Glu  Leu  Asp  Leu  Arg  Leu  Leu  Asp  Thr  Arg  Met  Cys  Asn  Asn  Ser
               145                      150                          155

Arg  Phe  Trp  Asn  Gly  Val  Leu  Thr  Asp  Ser  Met  Leu  Cys  Leu  Lys  Ala
               160                 165                          170

Gly  Ala  Lys  Gly  Gln  Ala  Pro  Cys  Lys  Gly  Asp  Ser  Gly  Gly  Pro  Leu
          175                  180                     185

Val  Cys  Gly  Lys  Gly  Lys  Val  Asp  Gly  Ile  Leu  Ser  Phe  Ser  Ser  Lys
     190                 195                          200

Asn  Cys  Thr  Asp  Ile  Phe  Lys  Pro  Thr  Val  Ala  Thr  Ala  Val  Ala  Pro
205                       210                     215                         220

Tyr  Ser  Ser  Trp  Ile  Arg  Lys  Val  Ile  Gly  Arg  Trp  Ser  Pro  Gln  Pro
               225                      230                          235

Leu  Thr
```

(2) INFORMATION FOR SEQ ID NO:3:

(i) SEQUENCE CHARACTERISTICS:
(A) LENGTH: 925
(B) TYPE: NUCLEIC ACID
(C) STRANDEDNESS: SINGLE
(D) TOPOLOGY: UNKNOWN (ii) MOLECULE TYPE:
(A) DESCRIPTION: OLIGONUCLEOTIDE (iii) HYPOTHETICAL: NO (iv) ANTI-SENSE: NO (vi) ORIGINAL SOURCE:
(A) ORGANISM: HUMAN ( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE: LOPEZ LGL LEUKEMIA
( I ) ORGANELLE:

( x i ) SEQUENCE DESCRIPTION:SEQ ID NO:3:

```
GATGGAGGCC TGCGTGTCTT CACTGCTGGT GCTGGCCCTG GGGGCCTGTC                    50

AGTAGGCAGC TCCTTTGGGA CCCAG ATC ATC GGG GGC CGG GAG                      93
                            Ile Ile Gly Gly Arg Glu
                            1             5

GTG ATC CCC CAC TCG CGC CCG TAC ATG GCC TCA CTG CAG                      132
Val Ile Pro His Ser Arg Pro Tyr Met Ala Ser Leu Gln
            10                  15

AGA AAT GGC TCC CAC CTG TGC GGG GGT GTC CTG GTG CAC                      171
Arg Asn Gly Ser His Leu Cys Gly Gly Val Leu Val His
20               25                  30

CCA AAG TGG GTG CTG ACG GCT GCC CAC TGC CTG GCC CAG                      210
Pro Lys Trp Val Leu Thr Ala Ala His Cys Leu Ala Gln
        35              40                      45

CGG ATG GCC CAG CTG AGG CTG GTG CTG GGG CTC CAC ACC                      249
Arg Met Ala Gln Leu Arg Leu Val Leu Gly Leu His Thr
                50                  55

CTG GAC AGC CCC GGT CTC ACC TTC CAC ATC AAG GCA GCC                      288
Leu Asp Ser Pro Gly Leu Thr Phe His Ile Lys Ala Ala
        60              65                  70

ATC CAG CAC CCT CGC TAC AAG CCC GTC CCT GCC CTG GTG                      327
Ile Gln His Pro Arg Tyr Lys Pro Val Pro Ala Leu Val
                75                  80

TTC GAC CTC GCG CTG CTT CAG CTG GAC GGG AAA GTG AAG                      366
Phe Asp Leu Ala Leu Leu Gln Leu Asp Gly Lys Val Lys
85                  90                  95

CCC AGC CGG ACC ATC CGG CCG TTG GCC CTG CCC AGT AAG                      405
Pro Ser Arg Thr Ile Arg Pro Leu Ala Leu Pro Ser Lys
        100                 105                 110

CAC CAG GTG GTG GCA GCA GGG ACT CGG TGC AGC ATG GCC                      444
His Gln Val Val Ala Ala Gly Thr Arg Cys Ser Met Ala
                115                 120

GGC TGG GGG CTG ACC CAC CAG GGC GGG GGC CTG TCC CGG                      483
Gly Trp Gly Leu Thr His Gln Gly Gly Gly Leu Ser Arg
125                 130                 135

GTG CTT GCG GAG CTG GAC CTC CAA GTG CTG GAC ACC CGC                      522
Val Leu Ala Glu Leu Asp Leu Gln Val Leu Asp Thr Arg
            140                 145

ATG TGT AAC AAC AGC CGC TTC TGG AAC GGC AGC CTC TCC                      561
Met Cys Asn Asn Ser Arg Phe Trp Asn Gly Ser Leu Ser
150                 155                 160

CCC AGC ATG GTC TGC CTG GCC GCC GAC TCC AAG GAC CAG                      600
Pro Ser Met Val Cys Leu Ala Ala Asp Ser Lys Asp Gln
            165                 170                 175

GCT CCC TGC AAG GGT GAC TCG GGC GGG CCC CTG GTG TGT                      639
Ala Pro Cys Lys Gly Asp Ser Gly Gly Pro Leu Val Cys
            180                 185

GGC AAA GGC CGG GTG TTG GCC GGA GTC CTG TCC TTC AGC                      678
Gly Lys Gly Arg Val Leu Ala Gly Val Leu Ser Phe Ser
        190                 195                 200

TCC AGG GTC TGC ACT GAC ATC TTC AAG CCT CCC GTG GCC                      717
Ser Arg Val Cys Thr Asp Ile Phe Lys Pro Pro Val Ala
            205                 210
```

| | | | | | | | | | | | | | | |
|---|---|---|---|---|---|---|---|---|---|---|---|---|---|---|
| ACC | GCT | GTG | GCG | CCT | TAC | GTG | TCC | TGG | ATC | AGG | AAG | GTC | | 756 |
| Thr | Ala | Val | Ala | Pro | Tyr | Val | Ser | Trp | Ile | Arg | Lys | Val | | |
| 215 | | | | 220 | | | | | 225 | | | | | |

| | | | | | | | | |
|---|---|---|---|---|---|---|---|---|
| ACC | GGC | CGA | TCG | GCC | TGATGCCTG | GGGTGATGGG | GACCCCCTCG | 801 |
| Thr | Gly | Arg | Ser | Ala | | | | |
| | | 230 | | | | | | |

CTGTCTCCAC AGGACCCTTC CCCTCCAGGG GTGCAGTGGG GTGGGTGAGG 851

ACGGGTGGGA GGGACAGGGA GGGACCAATA AATCATAATG AAGAAACGCT 901

CAAAAAAAAA AAAAAAAAAA AAAA 925

( 2 ) INFORMATION FOR SEQ ID NO:4:

( i ) SEQUENCE CHARACTERISTICS:
        ( A ) LENGTH: 232
        ( B ) TYPE: AMINO ACID
        ( D ) TOPOLOGY: UNKNOWN ( i i ) MOLECULE TYPE:
        ( A ) DESCRIPTION: PROTEIN ( i i i ) HYPOTHETICAL: YES ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: LOPEZ LGL LEUKEMIA
        ( I ) ORGANELLE:

( x i ) SEQUENCE DESCRIPTION:SEQ ID NO:4:

| | | | | | | | | | | | | | | |
|---|---|---|---|---|---|---|---|---|---|---|---|---|---|---|
| Ile | Ile | Gly | Gly | Arg | Glu | Val | Ile | Pro | His | Ser | Arg | Pro | Tyr | Met | Ala |
| 1 | | | | 5 | | | | | 10 | | | | | 15 |
| Ser | Leu | Gln | Arg | Asn | Gly | Ser | His | Leu | Cys | Gly | Gly | Val | Leu | Val | His |
| | | | 20 | | | | 25 | | | | | 30 | | |
| Pro | Lys | Trp | Val | Leu | Thr | Ala | Ala | His | Cys | Leu | Ala | Gln | Arg | Met | Ala |
| | | | 35 | | | | 40 | | | | 45 | | | |
| Gln | Leu | Arg | Leu | Val | Leu | Gly | Leu | His | Thr | Leu | Asp | Ser | Pro | Gly | Leu |
| | | 50 | | | | 55 | | | | | 60 | | | |
| Thr | Phe | His | Ile | Lys | Ala | Ala | Ile | Gln | His | Pro | Arg | Tyr | Lys | Pro | Val |
| 65 | | | | 70 | | | | 75 | | | | | 80 | |
| Pro | Ala | Leu | Val | Phe | Asp | Leu | Ala | Leu | Leu | Gln | Leu | Asp | Gly | Lys | Val |
| | | | | 85 | | | | 90 | | | | | 95 | |
| Lys | Pro | Ser | Arg | Thr | Ile | Arg | Pro | Leu | Ala | Leu | Pro | Ser | Lys | His | Gln |
| | | | 100 | | | | 105 | | | | 110 | | | |
| Val | Val | Ala | Ala | Gly | Thr | Arg | Cys | Ser | Met | Ala | Gly | Trp | Gly | Leu | Thr |
| | | 115 | | | | 120 | | | | | 125 | | | |
| His | Gln | Gly | Gly | Gly | Leu | Ser | Arg | Val | Leu | Ala | Glu | Leu | Asp | Leu | Gln |
| | 130 | | | | | 135 | | | | 140 | | | | |
| Val | Leu | Asp | Thr | Arg | Met | Cys | Asn | Asn | Ser | Arg | Phe | Trp | Asn | Gly | Ser |
| 145 | | | | | 150 | | | | 155 | | | | | 160 |
| Leu | Ser | Pro | Ser | Met | Val | Cys | Leu | Ala | Ala | Asp | Ser | Leu | Asp | Gln | Ala |
| | | | | 165 | | | | 170 | | | | 175 | | |
| Pro | Cys | Lys | Gly | Asp | Ser | Gly | Gly | Pro | Leu | Val | Cys | Gly | Lys | Gly | Arg |
| | | | 180 | | | | 185 | | | | 190 | | | |
| Val | Leu | Ala | Gly | Val | Leu | Ser | Phe | Ser | Ser | Arg | Val | Cys | Thr | Asp | Ile |
| | | 195 | | | | 200 | | | | | 205 | | | |

```
Phe Lys Pro Pro Val Ala Thr Ala Val Ala Pro Tyr Val Ser Trp Ile
    210                 215                 220

Arg Lys Val Thr Gly Arg Ser Ala
225                 230
```

( 2 ) INFORMATION FOR SEQ ID NO:5:

( i ) SEQUENCE CHARACTERISTICS:
        ( A ) LENGTH: 41
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: RAT
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE: CYTOLYTIC GRANULE
        ( H ) CELL LINE: RNK-16 LGL
        ( I ) ORGANELLE:

( i x ) FEATURE:
        ( A ) NAME/KEY:
        ( B ) LOCATION:
        ( C ) IDENTIFICATION METHOD:
        ( D ) OTHER INFORMATION: N indicates inosine (I)

( x i ) SEQUENCE DESCRIPTION:SEQ ID NO:5:

```
GAATTCTACA TGGTNTCNCT NCAAAACACN AAATCNGACG T          41
```

( 2 ) INFORMATION FOR SEQ ID NO:6:

( i ) SEQUENCE CHARACTERISTICS:
        ( A ) LENGTH: 41
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGNUCLEOTIDE ( i i i ) HYPOTHETICAL: NO ( i v ) ANTI-SENSE: NO ( v i ) ORIGINAL SOURCE:
        ( A ) ORGANISM: RAT
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE: CYTOLYTIC GRANULE
        ( H ) CELL LINE: RNK-16 LGL
        ( I ) ORGANELLE:

( i x ) FEATURE:
        ( A ) NAME/KEY:
        ( B ) LOCATION:
        ( C ) IDENTIFICATION METHOD:
        ( D ) OTHER INFORMATION: N is inosine (I).

( x i ) SEQUENCE DESCRIPTION:SEQ ID NO:6:

```
GAATTCTATA TGGTNTCNCT NCAGAATACN AAGTCNGATG T          41
```

( 2 ) INFORMATION FOR SEQ ID NO:7:

( i ) SEQUENCE CHARACTERISTICS:
        ( A ) LENGTH: 12
        ( B ) TYPE: AMINO ACID
        ( D ) TOPOLOGY: UNKNOWN ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: RAT
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE: CYTOLYTIC GRANULE
        ( H ) CELL LINE: RNK-16 LGL
        ( I ) ORGANELLE:

( x i ) SEQUENCE DESCRIPTION:SEQ ID NO:7:

Tyr Met Val Ser Leu Gln Asn Thr Lys Ser His Met
1              5                         10

( 2 ) INFORMATION FOR SEQ ID NO:8:

( i ) SEQUENCE CHARACTERISTICS:
        ( A ) LENGTH: 21
        ( B ) TYPE: NUCLEIC ACID
        ( C ) STRANDEDNESS: SINGLE
        ( D ) TOPOLOGY: UNKNOWN ( i i ) MOLECULE TYPE:
        ( A ) DESCRIPTION: OLIGNUCLEOTIDE ( i i i ) HYPOTHETICAL: NO ( i v ) ANTI-SENSE: YES ( v i ) ORIGINAL SOURCE:
        ( A ) ORGANISM: RAT
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE: CYTOLYTIC GRANULE
        ( H ) CELL LINE: RNK-16 LGL
        ( I ) ORGANELLE:

( x i ) SEQUENCE DESCRIPTION:SEQ ID NO:8:

GAATTCAGGC CCTCCAGAGT C    21

( 2 ) INFORMATION FOR SEQ ID NO:9:

( i ) SEQUENCE CHARACTERISTICS:
        ( A ) LENGTH: 5
        ( B ) TYPE: AMINO ACID
        ( D ) TOPOLOGY: UNKNOWN ( i i ) MOLECULE TYPE:
        ( A ) DESCRIPTION: PROTEIN ( i i i ) HYPOTHETICAL: NO ( v i ) ORIGINAL SOURCE:
        ( A ) ORGANISM: RAT
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:

( G ) CELL TYPE: CYTOLYTIC GRANULE
( H ) CELL LINE: RNK-16 LGL
( I ) ORGANELLE:

( x i ) SEQUENCE DESCRIPTION:SEQ ID NO:9:

Asp Ser Gly Gly Pro
1               5

( 2 ) INFORMATION FOR SEQ ID NO:10:

( i ) SEQUENCE CHARACTERISTICS:
( A ) LENGTH: 4
( B ) TYPE: AMINO ACID
( D ) TOPOLOGY: UNKNOWN ( i i ) MOLECULE TYPE:
( A ) DESCRIPTION: PROTEIN ( i i i ) HYPOTHETICAL: NO ( v i ) ORIGINAL SOURCE:
( A ) ORGANISM: RAT
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE: CYTOLYTIC GRANULE
( H ) CELL LINE: RNK-16 LGL
( I ) ORGANELLE:

( x i ) SEQUENCE DESCRIPTION:SEQ ID NO:10:

Ile Ile Gly Gly
1

( 2 ) INFORMATION FOR SEQ ID NO:11:

( i ) SEQUENCE CHARACTERISTICS:
( A ) LENGTH: 7
( B ) TYPE: AMINO ACID
( D ) TOPOLOGY: UNKNOWN ( i i ) MOLECULE TYPE:
( A ) DESCRIPTION: PROTEIN ( i i i ) HYPOTHETICAL: NO ( v i ) ORIGINAL SOURCE:
( A ) ORGANISM: RAT
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE: CYTOLYTIC GRANULE
( H ) CELL LINE: RNK-16 LGL
( I ) ORGANELLE:

( x i ) SEQUENCE DESCRIPTION:SEQ ID NO:11:

Val Leu Thr Ala Ala His Cys
1               5

( 2 ) INFORMATION FOR SEQ ID NO:12:

( i ) SEQUENCE CHARACTERISTICS:
( A ) LENGTH: 6
( B ) TYPE: AMINO ACID
( D ) TOPOLOGY: UNKNOWN ( i i ) MOLECULE TYPE:
( A ) DESCRIPTION: PROTEIN ( i i i ) HYPOTHETICAL: NO (vi) ORIGINAL SOURCE:
  (A) ORGANISM: RAT
  (B) STRAIN:
  (C) INDIVIDUAL ISOLATE:
  (D) DEVELOPMENTAL STAGE:
  (E) HAPLOTYPE:
  (F) TISSUE TYPE:
  (G) CELL TYPE: CYTOLYTIC GRANULE
  (H) CELL LINE: RNK-16 LGL
  (I) ORGANELLE:

(xi) SEQUENCE DESCRIPTION:SEQ ID NO:12:

Gly Asp Ser Gly Gly Pro
1               5